(12) United States Patent
Bathurst et al.

(10) Patent No.: US 6,306,398 B1
(45) Date of Patent: Oct. 23, 2001

(54) COMPOSITIONS WHICH INHIBIT APOPTOSIS, METHODS OF PURIFYING THE COMPOSITIONS AND USES THEREOF

(75) Inventors: Ian Cyril Bathurst, Kensington, CA (US); John D. Bradley, Brookline, MA (US); L. David Tomei, Richmond; Philip J. Barr, Berkeley, both of CA (US)

(73) Assignee: LXR Biotechnology, Inc., Richmond, CA (US)

( * ) Notice: Subject to any disclaimer, the term of this patent is extended or adjusted under 35 U.S.C. 154(b) by 0 days.

(21) Appl. No.: 08/862,765

(22) Filed: May 22, 1997

Related U.S. Application Data

(63) Continuation of application No. 08/467,035, filed on Jun. 6, 1995, now Pat. No. 5,635,187, which is a continuation-in-part of application No. 08/320,155, filed on Oct. 7, 1994, now Pat. No. 5,759,548, which is a continuation-in-part of application No. 08/158,980, filed on Nov. 30, 1993, now abandoned.

(51) Int. Cl.$^7$ .................................................. A61K 35/78
(52) U.S. Cl. ...................... 424/195.1; 435/325; 435/360; 435/410
(58) Field of Search .................... 424/195.1; 435/325, 435/360, 410

(56) References Cited

U.S. PATENT DOCUMENTS

| | | |
|---|---|---|
| 4,263,286 | 4/1981 | Nakajima et al. . |
| 4,340,586 | 7/1982 | Bekierkunst et al. . |
| 4,695,590 | 9/1987 | Lippman . |
| 4,746,652 | 5/1988 | Buckalew, Jr. et al. . |
| 4,793,996 * | 12/1988 | Kennedy et al. .................. 424/195.1 |
| 4,818,540 | 4/1989 | Chien et al. . |
| 4,938,961 | 7/1990 | Collins et al. . |
| 4,959,310 | 9/1990 | Brandon et al. . |
| 4,959,353 | 9/1990 | Brown et al. . |
| 5,053,327 | 10/1991 | Brandon et al. . |
| 5,093,505 | 3/1992 | Nishino et al. . |
| 5,130,298 | 7/1992 | Cini et al. . |
| 5,140,043 | 8/1992 | Darr et al. . |
| 5,217,717 | 6/1993 | Kennedy et al. . |
| 5,238,965 | 8/1993 | Piazza et al. . |
| 5,326,690 | 7/1994 | Xu et al. . |
| 5,330,972 | 7/1994 | Cope . |
| 5,340,568 | 8/1994 | Piazza et al. . |
| 5,636,187 | 6/1997 | Fujii et al. . |

FOREIGN PATENT DOCUMENTS

| | | |
|---|---|---|
| 0626177 | 11/1994 | (EP) . |
| 63-51335 | 3/1988 | (JP) . |
| WO 90/03574 | 4/1990 | (WO) . |
| WO 94/20121 | 9/1994 | (WO) . |
| WO 94/25621 | 11/1994 | (WO) . |

OTHER PUBLICATIONS

Dialog® Abstract of JP Patent No. 63–51335 (Mar. 4, 1988). One page total.

Ameisen et al., "Cell dysfunction and depletion in AIDS: The programmed cell death hypothesis" *Immunol. Today* (1991) 12(4):102–105.

Billings et al., "The interaction of the potato–derived chymotrypsin inhibitor with C3H/10T1/2 cells" *Carcinogenesis* (1991) 12(4):653–657.

Birk et al., "A pure trypsin inhibitor from soya beans" *Biochem. J.* (1963) 87:281–284.

Birk, "The Bowman–Birk inhibitor" *Int. J. Peptide Protein Res.* (1985) 25:113–131.

Bligh et al., "A rapid method of total lipid extraction and purification" *Can. J. Biochem. Physiol.* (1959) 37(8):911–917.

Chang et al., "Effects of protease inhibitors on c–Myc expression in normal and transformed C3H 10T1/2 cell lines" *Mol. Carcinogen.* (1990) 3:226–232.

Chien et al., "A simple technique for multiorgan preservation" *J. Thorac. Cardiovasc. Surg.* (1988) 95:55–61.

Chien et al., "A simple technique for producing supravalvular aortic stenosis in animals" *Cardiovascular Research* (1988) 22(10):739–745.

Chien et al., "New autoperfusion preparation for long–term organ preservation" *Circulation* (1988) 78 (suppl. III):III–58–III–65.

Chien et al., "The effect of hibernation induction trigger on heart survival time during hypothermic storage" *Hibernation Induction Trigger for Organ Preservation*, C. Kerkaporta, ed., R.G. Landes Company, (1993) Chapter 6, pp. 106–115.

Chien et al., "Hibernation induction trigger for organ preservation" *Medical Intelligence Unit* (1993) R.G. Landes Co., Austin, Texas. A title page and table of contents are enclosed.

Chou et al., "Non–selective inhibition of transformed cell growth by a protease inhibitor" *Proc. Natl. Acad. Sci. USA* (1974) 71(5):1748–1752.

Christie, *High–performance liquid chromatography and lipids*, Oily Press Ltd., 1987, Dundee, Scotland. A title page and table of contents are enclosed.

(List continued on next page.)

Primary Examiner—Leon B. Lankford, Jr.
(74) Attorney, Agent, or Firm—Sheridan Ross P.C.

(57) ABSTRACT

The present invention is to methods of obtaining plant–derived compositions that inhibit apoptosis, the compositions obtained thereby, compositions comprising the composition, and methods of use thereof.

36 Claims, 15 Drawing Sheets

OTHER PUBLICATIONS

Christie, *Gas chromatography and lipids: a practical guide*, Oily Press Ltd., 1989, Dundee, Scotland. A title page and table of contents are enclosed.

Cohen et al., "Apoptosis and programmed cell death in immunity" *Annu. Rev. Immunol.* (1992) 10:267–293.

Collins et al., "New organ preservation solutions" *Kidney International* (1992) 42:(suppl. 38):S–197–S–202.

Dawson et al., eds., *Data for Biochemical Research* (1986) 3rd ed., Clarendon Press, Oxford. A title page and table of contents are enclosed.

Domínguez–Bello et al., "Cytotoxicity in MA–104 cells and rumen protozoa of some phytotoxins and their effect on fermentation by faunated and defaunated rumen inocula" *J. Agric. Food Chem.* (1993) 41:2045–2050.

Duke et al., "IL–2 addiction: Withdrawal of growth factor activates a suicide program in dependent T cells" *Lymphokine Res.* (1986) 5(4):289–299.

Eichholtz et al., "The bioactive phospholipid lysophosphatidic acid is released from activated platelets" *Biochem. J.* (1993) 291:677–680.

Funk et al., "Effect of fiber, protein source and time of feeding on methotrexate toxicity in rats" *J. Nutr.* (1991) 121:1673–1683.

Funk et al., "Effect of soy products on methotrexate toxicity in rats" *J. Nutr.* (1991) 121:1684–1692.

Gerschenson et al., "Apoptosis: A different tpe of cell death" *FASEB J.* (1992) 6:2450–2455.

Gertler et al., "A comparative study of the nutritional and physiological significance of pure soybean trypsin inhibitors and of ethanol–extracted soybean meals in chicks and rats" *J. Nutr.* (1967) 91:358–370.

Hamilton et al., Lipid Analysis: A Practical Approach, Richwood et al. (eds.) IRL Press at Oxford University Press, 1992. A title page and table of contents are enclosed.

Hardy et al., "High–pH anion–exchange chromatography of glycoprotein–derived carbohydrates" *Meth. Enzymol.* (1994) 230:208–225.

Hasdai et al., "Growth, digestibility, and enzyme activities in the pancreas and intestines of guinea–pigs fed on raw and heated soya–bean flour" *Brit. J. Nutr.* (1989) 62:529–537.

Jungalwala, "Recent developments in techniques for phospholipid analysis" *Phospholipids in Nervous Tissues*, Eichenberg (ed.), John Wiley & Sons, 1985, pp. 1–44.

Kakade et al., "Contribution of trypsin inhibitors to the deleterious effects of unheated soybeans fed to rats" *J. Nutr.* (1973) 103:1772–1778.

Kanter et al., "Epidermal growth faactor and tumor promoters prevent DNA fragmentation by different mechanisms" *Biochem. Biophys. Res. Commun.* (1984) 118(12):392–399.

Kates, *Techniques of lipodology: Isolation, analysis and identification of lipids*, Burdon et al. (eds.), Elsevier. A title page and table of contents are enclosed.

Kennedy, "Prevention of carcinogenesis by protease inhibitors" *Cancer Res.* (Suppl.) (1994) 54:1999s–2005s.

Khayambashi et al., "Growth depression and pancreatic and intestinal changes in rats force–fed amino acid diets containing soybean trypsin inhibitor" *J. Nutr.* (1966) 89:455–464.

Kruman et al., "Apoptosis of murine BW 5147 thymoma cells induced by dexamethasone and γ–irradiation" *J. Cell. Physiol.* (1991) 148:267–273.

Moolenaar, "LPA: a novel lipid mediator with diverse biological actions" *TICB* (1994) 4:213–219.

Neely et al., "Effect of pressure development on oxygen consumption by isolated rat heart" *Am. J. Physiol.* (1967) 212:804–814.

Oates et al., "Cell death (apoptosis) during pancreatic involution after raw soya flour feeding in the rat" *Am. J. Physiol.* (1986) 250:G9–G14.

Patton et al., "Separation of phospholipids and individual molecular species of phospholipids by high–performance liquid chromatography" *J. Lipid Res.* (1982) 23:190–196.

Sambrook et al., eds., *Molecular Cloning. A Laboratory Manual* (1989) 2nd ed., vols. 1–3, Cold Spring Harbor Laboratory Press, Cold Spring Harbor, New York. A title page and table of contents are enclosed.

Schnebli et al., "Selective inhibition of growth of transformed cells by protease inhibitors" *Proc. Natl. Acad. Sci. USA* (1972) 69(12):3825–3827.

Sheppard et al., "The relationship between AIDS and immunologic tolerance" *J. AIDS* (1992) 5:143–147.

Simpson, "Stimulation of hypertrophy of cultured neonatal rat heart cells through an $\alpha_1$–adrenergic receptor and induction of beating through an $\alpha_1$– and $\beta_1$–adrenergic receptor interaction" *Cir. Res.* (1985) 56(6):884–894.

Singal, ed., *Oxygen radicals in the pathophysiology of heart disease*, Kluwer Academic Publishers, Boston, 1988. A title page and table of contents are enclosed.

Smetana et al., "Antimicrobial gentamicin activity in the presence of exogenous protease inhibitor (Bowman–Birk inhibitor) in gentamicin–induced nephrotoxicity in rats" *Nephron* (1992) 61:68–72.

Sojar et al., "Chemical deglycosylation of glycoproteins" *Meth. Enzymol.* (1987) 138:341–350.

Su–Fan et al., "A new technique for producing pure aortic stenosis in animals" *Am. J. Physiol.* (1984) 246 (Heart Circ. Physiol. 15):H296–H301.

Su–Fan et al., "Energy production, $O_2$ consumption, and blood flow reserve in experimental aortic valve disease" *Am. J. Physiol.* (1987) 252 (Heart Circ. Physiol. 21):H243–H251.

Takasaki et al., "Hydrazinolysis of asparagine–linked sugar chains to produce free oligosaccharides" *Meth. Enzymol.* (1982) 83:263–268.

Tomei et al., "Inhibition of radiation–induced apoptosis in vitro by tumor promoters" *Biochem. Biophys. Res. Commun.* (1988) 155(1):324–331.

Tomei et al., eds., *Apoptosis: The Molecular Basis of Cell Death* (1991) Cold Spring Harbor Laboratory Press, Cold Spring Harbor, New York. The title page and table of contents were previously submitted.

Troll et al., "Anticarcinogenic action of protease inhibitors" *Adv. Cancer Res.* (1987) 49:265–283.

van den Berg et al., "Hypochlorous acid–mediated modification of cholestoral and phospholipid: analysis of reaction products by gas chromatography–mass spectrometry" *J. Lipid. Res.* (1993) 34:2005–2012.

Vaughn et al., "Further evidence that lipoxygenase activity is required for arachidonic acid–elicited hypersensitivity in potato callus cultures" *Plant Sci.* (1992) 84:91–98.

Wicomb et al., "24-hour rabbit heart storage with UW solution. Effects of low-flow perfusion, colloid, and shelf storage" *Transplantation* (1989) 48:6–9.

Wicomb et al., "Comparison of cardioplegic and UW solutions for short-term rabbit heart preservation" *Transplantation* (1989) 47(4):733–734.

Wicomb et al., "Improved cardioplegia using new perfusates" *Transplantation Proceedings* (1989) 21(1):1357–1358.

Wicomb et al., "Optimal cardioplegia and 24-hour heart storage with simpified UW solution containing polyethylene glycol" *Transplantation* (1990) 49(2):261–264.

Wicomb et al., "Value of polyethylene glycol (PEG) and horseradish peroxidase (HRP) for hypothermic rabbit heart perfusion" *Transplantation Proceedings* (1989) 21(1):1366–1368.

Wu et al., "An anti–apoptotic compound improves hypothermic rabbit heart preservation" *American Society of Transplant Physicians*, Dallas, Texas, May 26–29, 1996, Abstract No. 310. An abstract submission form is submitted herewith.

Wu et al., "Enhancement of hypothermic rat liver preservation with an antiapoptotic compound" 22nd Annual Scientific Meeting of the American Society of Transplant Surgeons, Dallas, Texas, May 29–31, 1996, Abstract No. P–41. A letter of acceptance to the poster session is also included.

Wylie, "Glucocorticoid–induced thymocyte apoptosis is associated with endogenous endonuclease activation" *Nature* (1980) 284:555–556.

Yavelow et al., "Bowman–Birk soybean protease inhibitor as an anticarcinogen" *Cancer Res.* (Suppl.) (1983) 43:2454s–2459s.

Yavelow et al., "Nanomolecular concentrations of Bowman– Birk soybean protease inhibitor suppress x–ray–induced transformation in vitro" *Proc. Natl. Acad. Sci. USA* (1985) 82:5395–5399.

* cited by examiner

COMPOSITIONS WHICH INHIBIT APOPTOSIS, METHODS OF PURIFYING THE COMPOSITIONS AND USES THEREOF

This is a continuation of U.S. patent application Ser. No. 08/467,035, filed Jun. 6, 1995, U.S. Pat. No. 5,635,187, which is a continuation-in-part of U.S. patent application Ser. No. 08/320,155 filed Oct. 7, 1994, U.S. Pat. No. 5,759,548, which is a continuation-in-part of U.S. patent application Ser. No. 08/158,980, filed Nov. 30, 1993, now abandoned and incorporated herein by reference.

FIELD OF THE INVENTION

This invention relates to compositions of matter which are effective in inhibiting apoptotic cell death.

BACKGROUND OF THE INVENTION

Apoptosis is a normal physiologic process that leads to individual cell death. This process of programmed cell death is involved in a variety of normal and pathogenic biological events and can be induced by a number of unrelated stimuli. Changes in the biological regulation of apoptosis also occur during aging and are responsible for many of the conditions and diseases related to aging. Recent studies of apoptosis have implied that a common metabolic pathway leading to cell death may be initiated by a wide variety of signals, including hormones, serum growth factor deprivation, chemotherapeutic agents, ionizing radiation, and infection by human immunodeficiency virus (HIV). Wyllie (1980) *Nature* 284:555–556; Kanter et al. (1984) *Biochem. Biophys. Res. Commun.* 118:392–399; Duke and Cohen (1986) *Lymphokine Res.* 5:289–299; Tomei et al. (1988) *Biochem. Biophys. Res. Commun.* 155:324–331; and Kruman et al. (1991) *J. Cell. Physiol.* 148:267–273; Ameisen and Capron (1991) *Immunol. Today* 12:102–105; and Sheppard and Ascher (1992) *J. AIDS* 5:143–147. Agents that affect the biological control of apoptosis thus have therapeutic utility in numerous clinical indications.

Apoptotic cell death is characterized by cellular shrinkage, chromatin condensation, cytoplasmic blebbing, increased membrane permeability and internucleosomal DNA cleavage. Gerschenson et al. (1992) *FASEB J.* 6:2450–2455; and Cohen and Duke (1992) *Ann. Rev. Immunol.* 10:267–293.

All references cited herein both supra and infra are hereby incorporated herein by reference.

A variety of food supplements containing, in part, partially processed plant extracts have been used to ameliorate the gastrointestinal disorders that often accompany chemotherapy, radiation and AIDS. The supplements generally contain carbohydrates, fat and plant protein hydrolysates. See, e.g., Tomei and Cope et al. in Apoptosis The Molecular Basis of Cell Death (1991) Cold Spring Harbor Laboratory Press.

Several proteinase inhibitors derived from plant extracts have anticarcinogenic activity. Troll et al. (1987) *Adv. Cancer Res.* 49:265–283. The Bowman-Birk inhibitors are the best described of these inhibitors. Birk (1985) *Int. J. Pep. Pro. Res.* 25:113–131. Bowman-Birk inhibitors are described as a family of disulfide bonded proteins with a molecular weight of about 8 kD which suppress cellular transformation. Chou et al. (1974) *Proc. Natl. Acad. Sci. USA* 71:1748–1752; Yavelow et al. (1985) *Proc. Natl. Acad. Sci. USA* 82:5395–5399; and Yavelow et al. (1983) *Cancer Res. (Suppl.)* 43:2454s–2459s. Crude soybean extracts containing Bowman-Birk inhibitors have been described. Kennedy et al. U.S. Pat. No. 4,793,996; PCT publication No. WO 94/20121; and Kennedy, A. R. (1994) *Cancer Res.* (Suppl) 54:1999s–2005s. Bowman-Birk inhibitors have also been described immunologically. WO 90/03574; and U.S. Pat. Nos. 4,959,310; and 5,053,327. Bowman-Birk inhibitors have also been found to have activity in degranulation of macrophages. Japanese Patent No. 63051335.

Lysophosphatidic acid (LPA) is found in a variety of plant products as are a variety of phospholipids. LPA as been found to have a variety of physiological activities including mitogenesis, growth factor and as an anti-wrinkle agent. U.S. Pat. Nos. 4,263,286; 4,746,652; 5,326,690; and 5,340,568. LPA is reviewed in detail by Moolenaar (1994) *TICB* 4:213–219; and Eichholtz et al. (1990) *Biochem. J.* 291:677–680.

SUMMARY OF THE INVENTION

The present invention encompasses methods of obtaining compositions that inhibit apoptosis and the compositions obtained thereby. The compositions are termed phytogenic apoptosis inhibitors (PAIs). The invention encompasses physiologically acceptable compositions suitable for administering the PAIs in an amount sufficient to modulate apoptosis. The invention further encompasses methods of use of the PAIs.

MODES OF CARRYING OUT THE INVENTION

Figure 1:
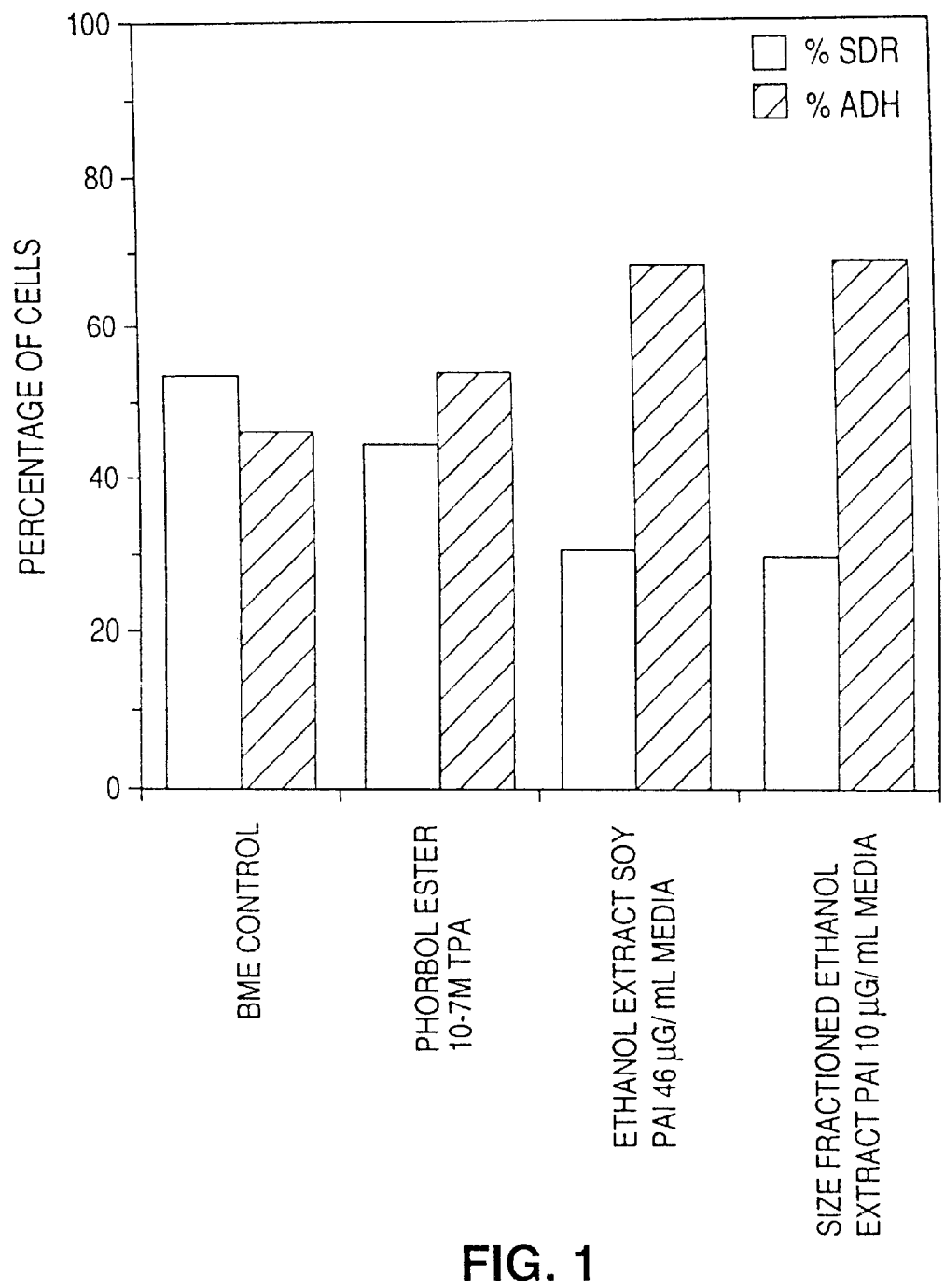
FIG. 1 presents the anti-apoptotic effect of PAIs on confluent C3H 10T½ cells.

It has now been found that a variety of plant constituents contain components which, when at least partially purified and purified, exhibit the ability to inhibit apoptosis. These compositions are readily separable from Bowman-Birk inhibitors and are distinct from other, known, therapeutically effective plant products. The composition may vary slightly in chemical constituents depending on the source and growing conditions of the plant from which they are derived. The compositions are referred to herein as "PAIs" as the invention encompasses related compositions made by the methods described herein but obtained from different plant sources. The composition may also be prepared synthetically by methods known in the lipid synthesis art. Several relatively purified compositions are provided and are designated L/G, AcE, MAcE and FAcE, to designate different degrees of purity as discussed below. Relatively pure fractions are also provided designated "D" and "L" as discussed below, each of which is a mixture of phospholipids. Two additional, relatively pure compositions are provided both of which contain lysophosphatidic acid (LPA); LPA and a protein carrier; and LPA and an otherwise inactive fraction "B."

PAIs can be isolated from a variety of different plants and plant organs. Preferably the plants are in the *leguminosae* (beans and peas etc.) family, but PAIs can be isolated from other plants such as those in the *solanum* (such as potatoes) and *allium* (such as garlic) families. PAIs can also be isolated from partially purified plant extracts including, but not limited to, molasses, lecithin, partially purified protein concentrates and partially purified protein hydrolysates. It is within the skill of one in the art, utilizing the methods described herein, to determine whether PAIs can be isolated from a particular species of plant, plant extract or organ within a plant.

Any plant extract or part thereof that yields the compositions is suitable for use in the present invention. The plant organs which can be utilized include, but are not limited to, stems, leaves, roots, flowers, rhizomes, and preferably, storage organs such as seeds, tubers and bulbs. Preferably, the plant part utilized is a storage organ including, but not limited to, potatoes, and garlic. Most preferably the dried seeds of legumes including, but not limited to, soybeans and peas are used for ease of processing. Although the terms "seed" and "seeds" are used herein, it should be understood that these terms encompass any plant part which yields at least one therapeutically active PAI, or PAI that is active in cell culture.

The invention encompasses methods for substantially purifying PAIs. Various degrees of purity can be achieved. The seeds are ground or pulverized, preferably into a powder or flour. As used herein, the term powder refers to a ground dried plant part. The powder particles should be sufficiently small enough to allow substantial surface area exposure to the various liquids to which they are exposed. Any method of grinding or pulverizing is suitable for use herein, typically grinding of seeds is accomplished by a commercial mill. PAIs are unusually heat stable, thus grinding can be done at temperatures that denature many proteins. Seed flours which are purchased commercially can also be used. For instance, soybean flour and various yellow and green pea flours have been found to contain active PAIs.

The seed powder is then delipidated by any method known in the art. It may be necessary to delipidate the powder in an inert environment, for example oxygen-free nitrogen or argon, or to include antioxidants during the procedure, for example BHT or BHA, to improve activity or minimize changes of an oxidative nature. Delipidation is generally accomplished by extracting the powder with a solution containing an organic solvent. Suitable organic solvents include, but are not limited to, acetone, carbon tetrachloride, ether, hexane and chloroform. Typically, the concentration of organic solvent in the solution is from 50–100%. Preferably, the organic solvent is acetone. The concentration of organic solution used may vary with respect to the particular solvent and the seed type; determination of the effective concentration is within the skill of one in the art. Preferably, in the case of acetone, the concentration is about 70%. Multiple organic extractions may also be carried out. Ratios of organic solution to powder (weight/volume) may also vary. Although not limited to the following range, typically the ratios are from about 2:1 to about 1:20 (weight powder/volume organic solution) are employed. In the case of acetone, a ratio of 1:5 is preferred.

Due to the stability of PAIs, the temperature and atmospheric pressure under which delipidation takes place are largely restricted only by the respective freezing and boiling points of the organic solutions employed. Typically, for ease of use, the delipidation takes place at room temperature and atmospheric pressure. The extraction time is likewise not stringent and depends largely upon the ratio of powder to organic solution. In the case of 70% acetone extraction with a ratio of 1:5, delipidation typically takes place for 30 minutes, with constant stirring.

The organic solution is then separated from the powder by any method known in the art. Preferably, the powder is removed from the organic phase by centrifugation and removal of the organic phase. Any all suitable form of separation can also be employed including, but not limited to, filtration or separation by gravity. The PAIs remain in the extracted powder.

The delipidated powder is then extracted with an aqueous solution to yield an aqueous retentate containing the PAIs. The aqueous solution can be a buffered solution such as phosphate buffered saline (PBS) and may also contain up to about 80% water miscible organic solvents. Suitable water miscible organic solvents include, but are not limited to, acetonitrile, lower alkanols, especially $C_1$–$C_4$ alkanols such as ethanol, methanol and propanol, lower alkanediols, especially $C_2$–$C_4$ alkanediols such as ethyleneglycol, and polymers of lower alkanediols, especially polyethyleneglycol. Preferably ethanol is used, most preferably at 50% concentration.

The ratio of aqueous solution to powder can also be varied. The extraction ratio may be from about 1:1 to at least about 1:20 (weight powder/volume aqueous solution). Generally, a 1:10 ratio of 50% ethanol is used. The extraction time varies also and depends on the volume of the aqueous solution and percentage of water miscible organic solvents used. In the case of a 1:10 volume of 50% ethanol, extraction proceeds for 1 hour with constant mixing or stirring (or agitation).

The pH range of the aqueous solution has been found to be largely irrelevant, ranges between 2.5 and 11 have been tested; it is thus likely that an even broader range may be effective. Typically, for ease of use, the pH range is 7–8.

The temperature and atmospheric conditions of the aqueous extraction can vary widely and depend largely on the freezing and boiling points of the aqueous solution. Typically, the extractions are carried out at room temperature and atmospheric pressure. Once the aqueous extraction has taken place, the aqueous retentate is removed for further processing. Any method of removal known in the art is suitable including but not limited to centrifugation and filtration.

The aqueous retentate is then further purified to yield the PAI. Any water-miscible organic solvent is removed by any method known in the art including but not limited to ultrafiltration, drying and dialysis. Ultrafiltration can be performed using a 10 kD molecular weight cut off to remove low molecular weight proteins such as monomers of the Bowman-Birk inhibitors and organic solvents. Likewise the molecular weight cut off of the dialysis tubing can be 10 kD.

Residual organic solvent can be removed by diafiltration after ultrafiltration or by multiple changes of the dialysate, for instance, by pure water. The aqueous retentate can be stored for up to several days in solution and indefinitely as a lyophilized solid. Preferably, the aqueous retentate is lyophilized. The lyophilized solid is ACE if the starting material is soy flour. Both the aqueous retentate and lyophilized retentate may be subject to further processing steps; the lyophilized retentate being resuspended in an appropriate aqueous solution prior to further processing.

Material obtained may be further separated by passage through any molecular weight size exclusion chromatography including, but not limited to, Sepharose S100HR (Pharmacia Biotechnology Piscataway N.J. USA) or BioGel P-100 (BioRad Laboratories Inc, Hercules Calif. USA) in an aqueous buffer. Suitable buffers include, but are not limited to, 0.1 to 0.3 M ammonium bicarbonate or 0.1 to 0.3 M NaCl in 10 to 50 mM phosphate at neutral pH.

The PAIs obtained from size exclusion chromatography are found in the void volume and have an apparent molecular weight of greater than 80 kD. The material found in this fraction may be resolved by sodium dodecyl sulfate polyacrylamide gel electrophoresis (SDS-PAGE) under reducing conditions and contains several proteins. Staining with Coomassie Blue indicates the presence of 6–8 proteins of a molecular weight range from 18 to 68 kD. Analysis by thin layer chromatography demonstrates the presence of several lipid-type compounds.

The fractions eluted from the chromatography with the greatest absorbance at 280 nm are coincident with the fractions containing the greatest biological activity. The biological activity separates from low molecular weight material and elutes in the void volume at a position that is consistent with that of a molecular weight of greater than 80 kD or an aggregate. This material may be concentrated, dialyzed, lyophilized and stored indefinitely in a lyophilized form. The lyophilized solid is FAcE, if the starting material is soy flour.

Solubilized PAIs can be precipitated with acetone at a concentration of 70% or more. However, treatment with various agents, including strong acids, destroy their activity. For instance, trifluoroacetic acid, hydrochloric acid, trichloroacetic acid and phenol destroy their activity. However, pH levels as low as 2.5 do not destroy activity, as 1% acetic acid does not affect the activity of PAIs.

The PAIs can be further isolated by extracting a freeze dried high molecular weight fraction obtained from defatted and ethanol extracted seed flour into a single phase mixture of chloroform:methanol:water (4:8:3). This is most conveniently done by dissolving the dried material in the water fraction, then adding methanol followed by chloroform, mixing and removing the pecipitate. This extraction yields a glycolipid/lipid/phospholipid fraction which retains PAI activity.

For example, 0.1 gEQ (the amount derived from 0.1 g of starting material) of the high molecular weight fraction (FAcE) was dissolved in 7.5 ml of water and with constant mixing, 20 ml of methanol was added followed by 10 ml of chloroform. The insoluble material was removed by centrifugation (8,000×g×10 min) and the PAI reclaimed from the solution by rotary evaporation to remove the organic solvents and freeze-drying to remove the water. The fraction obtained has been termed the L/G fraction. The carbohydrate composition of the L/G fraction consists of arabinose and galactose in a 3:2 ratio with fucose, rhamnose, glucosamine, glucose and mannose all present as minor constituents.

The L/G fraction can be further separated on the basis of its solubility in a mixture of chloroform:methanol and resolved by silica chromatography either in a chromatography column or by a thin-layer chromatography (TLC) plate format.

The material is then subjected to a preliminary chromatography step on silicic acid, i.e., a Mallinckrodt $SiO_2.xH_2O$ 100 mesh powder. The active material is loaded in chloroform and washed with chloroform or a chloroform:methanol mixture of 90:10 or 80:20 and eluted with methanol or $CHCl_3$:MeOH (10:90 or 20:80).

The active material can be further purified by chromatography on a diol column such as Diol SepPak cartridges (Waters, Millipore). For example, silica purified L/G, crude commercial lecithin, or other soy phospholipid preparations that are soluble in chloroform may be used as a starting material. For example, about 100–1000 mg of the sample is dissolved at a concentration of about 100 mg/ml in chloroform and loaded onto a pre-equilibrated 10 g diol column. The column is washed with 2–5 volumes of chloroform, eluted with 2–5 volumes of isopropanol, eluted with 2–5 volumes of ethanol, and, finally, eluted with 2–5 volumes of methanol. The majority of the activity is eluted in the methanol fraction although some activity is also found in the ethanol fraction. The activity may be isolated from methanol by drying. Suitable methods of drying include, but are not limited to, rotary evaporation or under vacuum. Some samples develop a precipitate upon overnight storage at −20° C; however, this precipitate can be removed by centrifugation without loss of activity.

The active material can be further separated by HPLC chromatography on a silica column such as Dynamax 60A Si column from Rainin Instrument Co., Inc. The gradient used to elute the active material is from 95:3:2 0.05 acetonitrile:methanol:water:ammonium hydroxide to 65:21:14 0.35 acetonitrile:methanol:water:ammonia hydroxide. The elution profile is monitored at 205 nm. As described in the Examples presented below, this stage of purification produces five separate products designated fractions 1–5. These products were isolated and analyzed separately for their composition and anti-apoptotic activity. Several fractions were recombined and assayed for their anti-apoptotic activity. It was found that the flow through contained predominantly lysophosphatidic acid (LPA), which, as described below, is a class of compounds. When assayed for activity, it was found that a commercially available LPA, L-a-lysophosphatidic acid, oleoyl (C18:1, [cis]-9), had no anti-apoptotic activity. LPA found in this fraction, and commercially available LPA in the presence of a protein or proteins to which it specifically binds, do possess anti-apoptotic activity. Thus, one embodiment of the present invention is compositions comprising LPA and an effective amount of a specific binding protein. Preferably, the binding protein is serum albumin. Note that the presence of Bowman-Birk inhibitors does not confer anti-apoptotic activity on LPA. It was also found that LPA in the presence of a fraction designated "B" also possessed anti-apoptotic activity. Fraction "B" primarily phosphatidyl inositol, does not possess anti-apoptotic activity. Thus another embodiment of the invention is a composition comprising LPA and an effective amount of fraction B or an active constituent thereof. Note that fraction B does not contain protein, thus the ability to induce anti-apoptotic activity in LPA is due solely to the presence of phospholipids. While not being bound by any one theory, the effect of fraction B may be due to the formation of a micelle or liposome which protects LPA and/or allows correct presentation of LPA to the cells.

Fraction "D" was also obtained and found to possess anti-apoptotic activity. This fraction corresponds to Peak 3 in Example 8. Thus another embodiment of the invention is compositions comprising fraction D.

Fraction "L" was also obtained and found to possess anti-apoptotic activity. This fraction corresponds to Peak 5 in Example 8. Thus another embodiment of the invention is compositions comprising fraction L. Fractions D and L may be additive in their anti-apoptotic activity. Thus another embodiment of the invention is compositions comprising fractions D and L.

Thus, the above embodiments are also included in the term PAI and are suitable for use in the indications and compositions described herein. LPA has the structure:

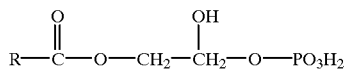

wherein R is an unsubstituted or substituted, saturated or unsaturated, straight or branched chain alkyl having from 11 to about 23 carbon atoms.

Also, as used herein, LPA encompasses a variety of molecules, including, but not limited to, a 2-deoxy- or 2-deoxy-2-halo-lysophosphatidic acid compound having the structure:

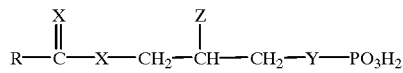

or a pharmaceutically-acceptable salt thereof, wherein —R is unsubstituted or substituted, saturated or unsaturated, straight or branched-chain alkyl having from 11 to about 23 carbon atoms; each X is independently O or S; Y is O or $CH_2$; and Z is H, halo, $NH_2$, SH, OH, or $OPO_3H_2$.

Also included is RC(O)O— being lauryl, myristyl, palmityl, stearyl, palmitoleyl, oleyl or linoleyl; more particularly, oleyl, palmitoleyl, myristyl, palmityl, or lauryl; especially myristyl or lauryl.

Pharmaceutically-acceptable salts of LPAs include, but are not limited to, alkali metal salts, such as sodium and potassium; alkaline earth metal salts, such as calcium and magnesium; non-toxic heavy metal salts; ammonium salts; trialkylammonium salts, such as trimethyl-ammonium and triethylammonium; and alkoxyammonium salts, such as triethanolammonium, tri(2-hydroxyethyl)ammonium, and tromethamine (tris(hydroxymethyl)aminomethane). Particularly preferred are calcium salts.

Preferred compounds useful as LPA in combination with a specific binding protein or fraction B include, but are not limited to, L and D 1-myristoyl-2-fluoro-2-deoxy-glycerol-3-phosphate, L and D 1-lauroyl-2-fluoro-2-deoxy-glycerol-3-phosphate, L and D 1-oleoyl-2-fluoro-2-deoxy-glycerol-3-phosphate, L and D 1-palmitoleoyl-2-fluoro-2-deoxy-glycerol-3-phosphate, L and D myristoyl-2-deoxy-glycerol-3-phosphate, L and D 1-lauroyl-2-chloro-2-deoxy-glycerol-3-phosphate, L and D 1-myristoyl-2-chloro-2-deoxy-glycerol-3-phosphate, and calcium salts thereof.

Other factors which may influence the activity of these compositions are chain length of LPA, presence of cholesterol, presence of micelles, liposomes, detergents, and emulsifying agents, and chain position in LPA, i.e., first or second carbon on the glycerol. In the case of micelles, liposomes and detergents, micelles and liposomes will cause an enhancement of activity whereas detergents or detergent-like molecules will cause a decrease in activity.

The active fractions obtained from HPLC silica chromatography may be further separated on the basis of their hydrophobicity, for instance by HPLC on a C18 column (Dynamax 60A, Rainin Instrument Co. Inc.) in a variety of methanol containing buffers, including, but not limited to, 100% methanol containing 800 mg/l ammonium acetate; 99% methanol containing 1 mM sodium phosphate pH 7.4; and 90% methanol, 10% sodium phosphate pH 7.4. The material is eluted isocratically in 90:10 methanol:5 mM $NaPO_4$ pH 7.4.

A variety of methods are known in the art for purifying and analyzing lipids. Any method known in the art may be used in the practice of the present invention provided it results in purification of an active fraction. For review, see Bligh and Dyer (1959) *Can. J. Biochem. Physiol.* 37:911–917; Patton et al. (1982) *J. Lipid Res.* 23:190–196; Jungalwala (1985) Recent Developments in Techniques for Phospholipid Analysis, in Phospholipids in Nervous Tissues (ed. Eichberg) John Wiley and Sons, pp. 1–44; Hamilton et al. (1992) in the series, A Practical Approach (Richwood et al. eds.) IRL Press at Oxford University Press; and Kates (1986) Techniques of Lipidology: Isolation, Analysis and Identification in Laboratory Techniques in Biochemistry and Molecular Biology (Burdon et al. eds.) Elsevier.

Typically, soy flour, or fractions thereof, is extracted by suspending in water (20% weight per volume in the case of flour) and adding two volumes of methanol and one volume of chloroform. This is a single phase and is stirred/mixed at room temperature for thirty minutes to one hour. To this mixture is added one volume of chloroform, mixed, and one volume of water. This forms two phases and the phases are separated by centrifugation or a separating funnel after first removing any solids (if flour has been used as the starting material). The activity is in the organic (bottom) phase.

The in vitro apoptosis inhibitory activity of the PAIs appears to be largely limited to actively proliferating cells; quiescent cells appear to be relatively unaffected.

The active components of the PAIs are highly stable in the presence of proteases. For instance, the PAIs have been treated with trypsin, chymotrypsin, papain, elastase, subtilisin, and proteinase K under conditions suitable for proteolysis but the proteases have no effect on their activity.

The invention further comprises therapeutic compositions comprising substantially purified PAIs. The level of purity necessary for the composition can be determined empirically and is within the skill of one in the art. The compositions are suitable for use in a variety of disorders, as described below, and in both human and veterinary applications.

The activity of the PAIs, as well as active fractions thereof obtained during the purification method can be measured in any anti-apoptosis assay known in the art. These include, but are not limited to, the serum deprivation of the C3H 10O1/2 cell assay described in detail in commonly owned PCT Publication No. WO 9425621 which is the preferred assay method, as well as the methods described in Examples 3 and 4. Furthermore, in vivo apoptosis inhibition may be measured by any method known in the art.

In general, PAIs are pharmaceutically acceptable due to their low toxicity in the therapeutic dosage range, stability and ability to be incorporated into a wide variety of vehicles for numerous routes of administration. The PAIs can be administered alone or in combination with other pharmaceutically effective agents including, but not limited to, antibiotics, wound healing agents, antioxidants and other therapeutic agents. Suitable antibiotics include, but are not limited to, ampicillin, tetracycline, chloramphenicol and penicillin. Suitable wound healing agents include, but are not limited to, transforming growth factors (TGF-βs), epidermal growth factors (EGFs), fibroblast growth factors (FGFs) and platelet-derived growth factors (PDGFs). Suitable antioxidants include, but are not limited to, vitamins C and E.

The compositions contain at least a therapeutically effective amount of at least one PAI and may contain at least one physiologically acceptable carrier. A physiologically acceptable carrier is one that does not cause an adverse physical reaction upon administration and one in which PAIs are sufficiently soluble to deliver a therapeutically effective amount of the compound. The therapeutically effective amount of PAIs depends in part upon the manner of introduction and the indication to be treated and other criteria evident to ordinary skill of one in the art. Typically, a therapeutically effective amount is one sufficient to modulate apoptosis in the condition being treated as evidenced by amelioration of the symptoms. Typically, a therapeutically effective amount is from about 0.5–100% by weight of at least one PAI. The route(s) of administration useful in a particular indication are discussed below and are well known to one of skill in the art.

Routes of administration include, but are not limited to, topical, transdermal, parenteral, gastrointestinal, transbronchial and transalveolar. Topical administration is accomplished via a topically applied cream, gel, rinse, etc. containing therapeutically effective amounts of PAIs. Transdermal administration is accomplished by application of a cream, rinse, gel, etc. capable of allowing the PAIs to penetrate the skin and enter the blood stream. Parenteral routes of administration include, but are not limited to, direct injection such as intravenous, intramuscular, intraperitoneal or subcutaneous injection. Gastrointestinal routes of administration include, but are not limited to, ingestion and rectal. Transbronchial and transalveolar routes of administration include, but are not limited to, inhalation, either via the mouth or intranasally and direct injection into an airway, such as through a tracheotomy.

While the PAIs can be topically administered alone, it may be desirable to administer them in admixture with a topical pharmaceutically or cosmetically acceptable carrier. "Topical pharmaceutically acceptable carrier" as used herein is any substantially non-toxic carrier conventionally usable for topical administration of pharmaceuticals in which the PAIs will remain stable and bioavailable when applied directly to skin or mucosal surfaces. For example, the PAIs can be dissolved in a liquid, dispersed or emulsified in a medium in a conventional manner to form a liquid preparation or mixed with a semi-solid (gel) or solid carrier to form a paste, powder, ointment, cream, lotion or the like.

Suitable topical pharmaceutically acceptable carriers include water, petroleum jelly (vaseline), petrolatum, mineral oil, vegetable oil, animal oil, organic and inorganic waxes, such as microcrystalline, paraffin and ozocerite wax, natural polymers, such as xanthanes, gelatin, cellulose, collagen, starch, or gum arabic, synthetic polymers, such as discussed below, alcohols, polyols, and the like. The carrier may be a water miscible carrier composition that is substantially miscible in water. Such water miscible topical pharmaceutically acceptable carrier composition can include those made with one or more appropriate ingredients set forth above but can also include sustained or delayed release carriers, including water containing, water dispersible or water soluble compositions, such as liposomes, microsponges, microspheres or microcapsules, aqueous base ointments, water-in-oil or oil-in-water emulsions, gels or the like.

In one embodiment of the invention, the topical pharmaceutically acceptable carrier comprises a sustained release or delayed release carrier. The carrier is any material capable of sustained or delayed release of the PAIs to provide a more efficient administration resulting in one or more of less frequent and/or decreased dosage of the PAIs, ease of handling, and extended or delayed effects on dermatologic conditions. The carrier is capable of releasing the PAIs when exposed to any oily, fatty, waxy, or moist environment on the area being treated or by diffusing or by release dependent on the degree of loading of the PAIs to the carrier in order to obtain releases of the PAIs. Non-limiting examples of such carriers include liposomes, microsponges, microspheres, or microcapsules of natural and synthetic polymers and the like. Examples of suitable carriers for sustained or delayed release in a moist environment include gelatin, gum arabic, xanthane polymers; by degree of loading include lignin polymers and the like; by oily, fatty or waxy environment include thermoplastic or flexible thermoset resin or elastomer including thermoplastic resins such as polyvinyl halides, polyvinyl esters, polyvinylidene halides and halogenated polyolefins, elastomers such as brasiliensis, polydienes, and halogenated natural and synthetic rubbers, and flexible thermoset resins such as polyurethanes, epoxy resins and the like. Preferably, the sustained or delayed release carrier is a liposome, microsponge, microsphere or gel.

The compositions used in the method of treating dermatologic conditions of the invention are applied directly to the areas to be treated. While not required, it is desirable that the topical composition maintain the PAIs at the desired location for about 24 to 48 hours.

If desired, one or more additional ingredients conventionally found in topical pharmaceutical or cosmetic compositions can be included with the carrier: such as a moisturizer, humectants, odor modifier, buffer, pigment, preservative, vitamins such as A, C and E, emulsifier, dispersing agent, wetting agent, odor-modifying agent, gelling agents, stabilizer, propellant, antimicrobial agents, sunscreen, enzymes and the like. Those of skill in the art of topical pharmaceutical formulations can readily select the appropriate specific additional ingredients and amounts thereof. Suitable non-limiting examples of additional ingredients include superoxide dismutase, stearyl alcohol, isopropyl myristate, sorbitan monooleate, polyoxyethylene stearate, propylene glycol, water, alkali or alkaline earth lauryl sulfate, methylparaben, octyl dimethyl-p-amino benzoic acid (Padimate O), uric acid, reticulin, polymucosaccharides, hyaluronic acids, aloe vera, lecithin, polyoxyethylene sorbitan monooleate, vitamin A or C, tocopherol (vitamin E), alpha-hydroxy of alpha-keto acids such as pyruvic, lactic or glycolic acids, or any of the topical ingredients disclosed in U.S. Pat. Nos. 4,340,586, 4,695, 590, 4,959,353 or 5,130,298 and 5,140,043.

Because dermatologic conditions to be treated may be visible, the topical carrier can also be a topical cosmetically acceptable carrier. By "topical cosmetically acceptable carrier" as used herein is meant any substantially non-toxic carrier conventionally usable for topical administration of cosmetics in which the PAIs will remain stable and bioavailable when applied directly to the skin surface. Suitable cosmetically acceptable carriers are known to those of skill in the art and include, but are not limited to, cosmetically acceptable liquids, creams, oils, lotions, ointments, gels, or solids, such as conventional cosmetic night creams, foundation creams, suntan lotions, sunscreens, hand lotions, make-up and make-up bases, masks and the like. Thus, to a substantial extent topical cosmetically acceptable carriers and pharmaceutically acceptable carriers are similar, if not often identical, in nature so that most of the earlier discussion on pharmaceutically acceptable carriers also applies to cosmetically acceptable carriers. The compositions can contain other ingredients conventional in cosmetics including perfumes, estrogen, vitamins A, C or E, alpha-hydroxy or alpha-keto acids such as pyruvic, lactic or glycolic acids, lanolin, vaseline, aloe vera, methyl or propyl paraben, pigments and the like.

The effective amount of the PAIs in the compositions used to treat dermatologic conditions or diseases can vary depending on such factors as condition of the skin, age of the skin, the particular PAI or degree of the purity of the PAIs employed, the type of formulation and carrier ingredients used, frequency of administration, overall health of the individual being treated and the like. The precise amount for any particular patient use can be determined by those of skill in the pharmaceutical art taking into consideration these factors and the present disclosure. Preferably the composition is administered in at least two doses and no more than about six doses per day, or less when a sustained or delayed release form is used.

The compositions for topical administration usually contain from about 0.0001% to about 90% by weight of the PAIs compared to the total weight of the composition, preferably from about 0.5% to about 20% by weight of the PAIs to composition, and especially from about 2% to about 5% by weight of the PAIs to the composition.

The topical composition is administered by applying a coating or layer to the skin or mucosal area desired to be treated. As a practical matter of convenience, the applied material is rubbed into the area. Applications need not be rubbed into the skin and the layer or coating can be left on the skin overnight.

The present invention provides compositions suitable for transdermal administration including, but not limited to, pharmaceutically acceptable lotions, suspensions, oils, creams, ointments, rinses, gels and liposomal carriers suspended in a suitable vehicle in which a therapeutically effective amount of PAIs has been admixed. Such compositions are applied directly to the skin or incorporated into a protective carrier such as a transdermal device (so-called "patch"). Examples of suitable creams, ointments etc. can be found, for instance, in the Physician's Desk Reference. Examples of suitable transdermal devices are described, for instance, in U.S. Pat. No. 4,818,540 (Chien et al.).

The present invention includes compositions of PAIs suitable for parenteral administration including, but not limited to, pharmaceutically acceptable sterile isotonic solutions. Such solutions include, but are not limited to, saline and phosphate buffered saline for intravenous, intramuscular, intraperitoneal or subcutaneous injection of PAIs.

The present invention includes compositions of PAIs suitable for gastrointestinal administration including, but not limited to, pharmaceutically acceptable powders, pills or liquids for ingestion and suppositories for rectal administration.

The present invention includes compositions of PAIs suitable for transbronchial and transalveolar administration including, but not limited to, various types of pharmaceutically acceptable aerosols for inhalation. An example of a drug administered in the form of an aerosol is pentamidine which is administered to AIDS patients by inhalation to prevent pneumonia caused by *Pneumocystis carnii*.

The present invention further encompasses devices suitable for transbronchial and transalveolar administration of PAIs. Such devices include, but are not limited to, atomizers and vaporizers. The present invention also includes devices for electrical or direct injection. Electrical injection, or iontophoresis, is the process of using a small electrical current to drive charged elements, compounds and drugs through the skin for the purpose of delivering the therapeutic compound to the local tissues or to the whole body without breaking the skin.

The present invention further encompasses solutions suitable for storage of organs prior to transplantation. Suitable solutions are described in Chien et al. (1993) "Hibernation Induction Trigger for Organ Preservation" in Medical Intelligence Unit, R.G. Landes Co. Austin, Tex. PAIs ca be used, for instance, to replace much more impure soy preparations currently in use (e.g., Soyacal).

The above-mentioned compositions are meant to describe, but not limit, the compositions suitable for administering the PAIs of the invention. The methods of producing the various compositions are within the ability of one skilled in the art and are not described in detail here.

The methods of producing suitable devices for injection, topical application, atomizers and vaporizers are known in the art and will not be described in detail.

The invention further provides methods of treating apoptosis comprising administering an amount of the PAIs effective to inhibit apoptosis. Various apoptosis-related indications can be treated by the method including, but not limited to, dermatological effects of aging, disorders and diseases, immunosuppression, gastrointestinal perturbations, cardiovascular disorders, rejection of tissue transplantation, and Alzheimer's disease.

It has now been found that PAIs may be topically applied to the skin to treat a variety of dermatologic conditions. These conditions include, but are not limited to, wrinkling or sagging due to age and/or photodamage, psoriasis. The present invention thus encompasses methods of treating dermatological conditions. Furthermore, baldness may be caused by apoptosis of the cells of the hair follicles. Therefore, the PAIs would be suitable for use in topical treatment of the skin to prevent continued hair loss.

As discussed above, these conditions are preferably treated by topical application of a composition comprising an effective amount of PAIs. An effective amount of PAI is one which ameliorates or diminishes the symptoms of the dermatologic conditions. Preferably, the treatment results in resolution of the dermatologic condition or restoration of normal skin function; however, any amelioration or lessening of symptoms is encompassed by the invention.

Immunosuppression related disorders are caused by a variety of stimuli which include, but are not limited to, viruses including, but not limited to, HIV, chemotherapeutic agents, and radiation. These stimuli trigger apoptosis in a variety of disorders, including, but not limited to, those of the digestive tract tissues and associated gastrointestinal perturbations.

Gastrointestinal perturbations include, but are not limited to, damage to the lining of the gut, severe chronic ulcers, colitis, radiation induced damage, chemotherapy induced damage, and the perturbation of the gastrointestinal tract caused by parasites, and diarrhea from any other cause. Various viral and bacterial infections are known to result in gastrointestinal perturbations; the PAIs are also suitable for use in treatment of the side effects associated with these infections. PAIs are particularly suited for use in ameliorating the gastrointestinal disturbances associated with chemotherapy. As shown in the Examples presented below, rats treated with methotrexate and various PAIs suffered less feeding problems and had none of the diarrhea found in the control animals. Thus, PAIs are suitable for use not only in preventing the diarrhea associated with chemotherapy but also the nausea.

The PAIs are particularly suited to treatment of various gastrointestinal conditions in animals, particularly cattle. Such conditions, particularly diarrhea, account for the loss of many calves. Treatment of gastrointestinal conditions is preferably by gastrointestinal administration. In the case of cattle, an effective amount of the PAIs can be conveniently mixed in with the feed. In humans, administration can be by any method known in the art of gastrointestinal administration.

In addition, the PAIs can be administered to immunodeficient patients, particularly HIV-positive patients, to prevent or at least mitigate apoptotic death of T cells associated with the condition, which results in the exacerbation of immunodeficiencies as seen in patients with full blown AIDS. Preferably, administration of PAIs to such patients is parenterally, but may also be transdermal or gastrointestinally.

The PAIs can also be administered to treat apoptosis associated with reperfusion damage involved in a variety of conditions, including, but not limited to, coronary artery obstruction; cerebral infarction; spinal/head trauma and concomitant severe paralysis; reperfusion damage due to other insults such as frostbite; and any indication previously thought to be treatable by superoxide dismutase (SOD). For review of the effect of oxygen radicals in heart disease, see Singal (1988) "Oxygen Radicals in the Pathophysiology of Heart Disease" Kluwer Academic Publishers, MA, USA.

Myocardial and cerebral infarctions are caused generally by a sudden insufficiency of arterial or venous blood supply due to emboli, thrombi, or pressure that produces a macroscopic area of necrosis; the heart, brain, spleen, kidney, intestine, lung and testes are likely to be affected. Apoptosis occurs to tissue surrounding the infarct upon reperfusion of blood to the area; thus, PAIs are effective if administered at the onset of the infarct, during reperfusion, or shortly thereafter.

Thus, the invention includes methods of treating apoptosis associated with reperfusion comprising administering a therapeutically effective amount of at least one PAI to a patient in need of such therapy.

The invention further encompasses a method of reducing the apoptosis and reperfusion damage associated with myocardial and cerebral infarctions for patients with a high risk of heart attack and stroke by administering a therapeutically effective amount of at least one PAI to a patient in need of such therapy.

Preferably, treatment of reperfusion damage is by parenteral administration of the compositions of the invention. Any other suitable method may be used, however, for instance, direct cardiac injection in the case of myocardial infarct. Devices for such injection are known in the art, for instance the Aboject cardiac syringe.

The invention further provides methods of limiting and preventing apoptosis in cells during the culture or maintenance of mammalian organs, tissues, and cells by the addition of an effective amount of PAIs to any media or solutions used in the art of culturing or maintaining mammalian organs, tissues, and cells.

The invention further encompasses media and solutions known in the art of culturing and maintaining mammalian organs, tissues and cells, which comprise an amount of at least one PAI effective to limit or prevent apoptosis of the cells in culture.

These aspects of the invention encompass mammalian cell culture media comprising an effective amount of at least one PAI and the use of such media to limit or prevent apoptosis in mammalian cell culture. PAIs have been found to limit or prevent apoptosis under circumstances in which cells are subjected to mild traumas which would normally stimulate apoptosis. Such traumas may include, but are not limited to, low level irradiation, thawing of frozen cell stocks, rapid changes in the temperature, pH, osmolarity, or ion concentration of culture media, prolonged exposure to non-optimal temperature, pH, osmolarity, or ion concentration of the culture media, exposure to cytotoxins, disassociation of cells from an intact tissue in the preparation of primary cell cultures, serum deprivation (or growth in serum-free media).

Thus the invention encompasses compositions comprising tissue culture medium and an effective amount of at least one PAI. Serum-free media to which PAIs may be added as anti-apoptotic media supplements include, but are not limited to, AIM V® Media, Neuman and Tytell's Serumless Media, Trowell's T8 Media, Waymouth's MB 752/1 and 705/1 Media, and Williams' Media E. In addition to serum-free media, suitable mammalian cell culture media to which PAIs may be added as anti-apoptotic media supplements include, but are not limited to, Basal Eagle's Media, Fischer's Media, McCoy's Media, Media 199, RPMI Media 1630 and 1640, Media based on F-10 & F-12 Nutrient Mixtures, Leibovitz's L-15 Media, Glasgow Minimum Essential Media, and Dulbecco's Modified Eagle Media. Mammalian cell culture media to which PAIs may be added further comprise any media supplement known in the art, including but not limited to, sugars, vitamins, hormones, metalloproteins, antibiotics, antimycotics, growth factors, lipoproteins and sera.

The invention further encompasses solutions for maintaining mammalian organs prior to transplantation, which comprise an effective amount of at least one PAI, and the use of such solutions to limit or prevent apoptosis in such mammalian organs during their surgical removal and handling prior to transplantation. In all cases concentrations of PAIs required to limit or prevent apoptosis can be determined empirically by one skilled in the art by methods like those found in Examples 2, 3 and 4, as well as other methods known in the art.

It has also been found that the PAI fractions above a certain concentration can form micelles in solution. The invention thus includes compositions comprising micelles.

The following examples are provided to illustrate but not limit the invention.

EXAMPLE 1

PAI Isolation and Purification

Approximately 100 g of commercially available soybean flour (Sigma Chemical Co. St. Louis, Mo. USA and Central Soya, Archer Daniel Midlands) was suspended in 500 ml of 70% acetone and stirred at room temperature for 30 minutes. The delipidated soybean flour was recovered by centrifugation at 1,500 g for 10 minutes. This material was resuspended in 1 l of 50% ethanol and stirred at room temperature for 30 minutes. The supernatant, the aqueous retentate, was reclaimed by centrifugation at 1,500 g for 10 minutes.

The aqueous retentate was concentrated by ultrafiltration and the ethanol was removed by diafiltration over a 10 kD membrane (Amicon Beverly Mass. USA). This material was then loaded directly onto Sepharose S100HR (Pharmacia Biotechnology, Inc. Piscataway, N.J., USA) equilibrated in 10 mM ammonium bicarbonate. The peak of $A_{280}$ absorbing material eluted in the void volume and was pooled and lyophilized. The freeze-dried high molecular weight material was extracted into a single phase mixture of chloroform:methanol:water (3:8:4) by adding the single phase mixture to the dried material and mixing at room temperature for 30 minutes. The mixture was then centrifuged to remove the insoluble material. The insoluble material yielded a lipid/glycolipid fraction which retained PAI activity. This fraction has been termed the L/G fraction. The carbohydrate composition of the L/G fraction consists of arabinose and galactose in a 3:2 ratio with fucose, rhamnose, glucosamine, glucose and mannose all present as minor constituents. The carbohydrate composition was determined as described in Example 5.

The L/G fraction can be further separated on the basis of its solubility in a mixture of chloroform:methanol (80:20) and chromatography on silica (Silicic Acid 100 mesh, Mallinckrodt Chemical, Inc. KY). The silica chromatography is resolved in methanol to yield an active fraction (SiMe).

For a detailed summary of the physical and chemical characteristics of the soy flour extract at various stages of purification see Table 1, where ND stands for "none detected".

In Table 1, the activities and physical characteristics of the products of four stages of purification were determined. These four stages were: aqueous retentate; 70% acetone extract; 50% ethanol extract of the 70% acetone pellet; and the high molecular weight fraction purified by size exclusion gel filtration chromatography from the 50% ethanol fraction. Protein yield is expressed as protein recovered per gram dry weight of starting material, as measured by the Bradford assay procedure (BioRad Laboratories). Anti-apoptotic activity is expressed as the calculated concentration of material (µg/ml of media) required to save 50% of the cells released on serum free treatment as described in Example 2. Trypsin inhibition is expressed in relative units per µg of protein in the sample. A relative unit (U) was defined as the amount of inhibitory activity which decreases by 50% the initial rate of hydrolysis of a 100 µM substrate by 2 µg of trypsin in a total volume of 1 ml. Absorbance values at 260 and 280 nm are expressed per gram of starting material in a 1 ml cell. This gives an indication of relative protein and nucleic acid concentrations present. The ratio of 260/280 was used to estimate the amount of nucleic acid present as described in Dawson et al., Data for Biochemical Research, Third Edition, 1990 published Oxford Science Publications.

TABLE 1

Physical Characterization of Soy PAI Extract at Various Stages of Purification

| | Protein Concentration | Anti-apoptotic Activity | Trypsin Inhibition | Nucleic A280 | A260 | Acid |
|---|---|---|---|---|---|---|
| Soy Flour Water Extract | 196 mg/gm | Inhibitory | 0.561 U/µg | 116/gm | 134/gm | 2.4% |
| Soy Flour 70% Acetone Extract | 140 µg/gm | Inhibitory | ND | 4.5/gm | 7.2/gm | 11% |
| Soy Flour Acetone Pellet 50% Ethanol Extract (AcE) | 310 µg/gm | 11 µg/ml | 177 U/µg | 32/gm | 36/gm | ND |
| Soy Flour Acetone Pellet 50% Ethanol Gel Filtration Pool (FAcE) | 62 µg/gm | 0.14 µg/ml | 3.5 U/µg | 10/gm | 12/gm | ND |
| Soy Flour Acetone Pellet 50% Ethanol Gel Filtration Pool Organic Extract (L/G) | 20 µg/gm | 45 ng/ml | ND | 8.4/gm | 9.1/gm | ND |
| Soy Flour Acetone Pellet 50% Ethanol | 0.9 µg/gm | 12 ng/ml | ND | 6.55/gm | 7.7/gm | ND |

TABLE 1-continued

Physical Characterization of Soy PAI Extract at Various Stages of Purification

| | Protein Concentration | Anti-apoptotic Activity | Trypsin Inhibition | Nucleic A280 | A260 | Acid |
|---|---|---|---|---|---|---|
| Gel Filtration Pool | | | | | | |
| Organic Extract | | | | | | |
| Silicic acid Methanol Eluate (SiMe) | | | | | | |

EXAMPLE 2

Apoptosis Assay with C3H 10T½ Cells

In order to determine the apoptotic activity of the PAIs, the following experiment was performed. The cell assay is described in PCT Publication No. WO 9425621. Briefly, the cells, C3H 10T½ clone 8, were assayed at confluence (FIG. 1), during exponential growth phase when cell cycle position is randomly distributed with no cells arrested in $G_o$ (FIGS. 2 and 3), and in quiescence (FIG. 4). Exponential growth phase was assured by seeding at 2000 cells per 1 ml (5 ml for a 60 mm culture plate) five days prior to the beginning of the experiment. At T=0, cultures were transferred to serum-free medium, as an apoptosis stimulus, and seed extracts were added. Controls included $10^{-7}$ M 12-O-tetradecanoyl phorbol-13-acetate (TPA) to ensure the responsiveness of the cell culture. The PAI samples prepared by extraction with ethanol and by gel filtration were added to serum free medium at 0.1 g dry weight equivalents and sterile filtered prior to addition to the cultures. Assays were performed in triplicate or quadruplicate. Analyses of the cell responses were made after between 22 and 28 hours of serum deprivation and/or treatment with soy flour derived PAIs. Two assays were performed on each cell culture plate consisting of differential cell counts.

1. All non-adherent or loosely adherent cells were removed from the culture dish and counted by appropriate techniques, typically counting by electric particle counting instrument. These are the apoptotic cells, the serum deprived released cells (SDR), released by the action of cultivation in serum-free medium. Approximately 95% of these released cells are apoptotic as shown by both ultrastructure analysis and DNA fragmentation analysis.

2. The remaining adherent cells (ADH) are exposed to a buffered, typically pH 7.3, balanced salt solution such as Hanks Balanced Salt Solution without calcium and magnesium salts containing 0.05% trypsin and 0.53 mM ethylenediaminetetraacetic acid (EDTA). Each culture is incubated at either room temperature or 37° C. on a rocking platform to ensure uniform distribution of the trypsin reagent over the culture surface. After a standardized period of time, typically 10 minutes, the released cells are removed from each culture dish and measured by the same means as described above, typically electronic particle counting. This ADH cell count is comprised of both trypsin resistant and trypsin sensitive cells as described in PCT Publication No. WO 9425621.

The results obtained from the apoptosis cell assays are presented in FIGS. 1, 2, 3 and 4. In FIG. 1 the percentage of cells having undergone apoptosis (SDR) and adherent cells (ADH) are presented separately. The Data in FIG. 1 demonstrate that the PAIs are effective in reducing apoptosis in confluent cells, as compared with the Basal Medium Eagle (BME), serum-deprived control.

Figure 2:
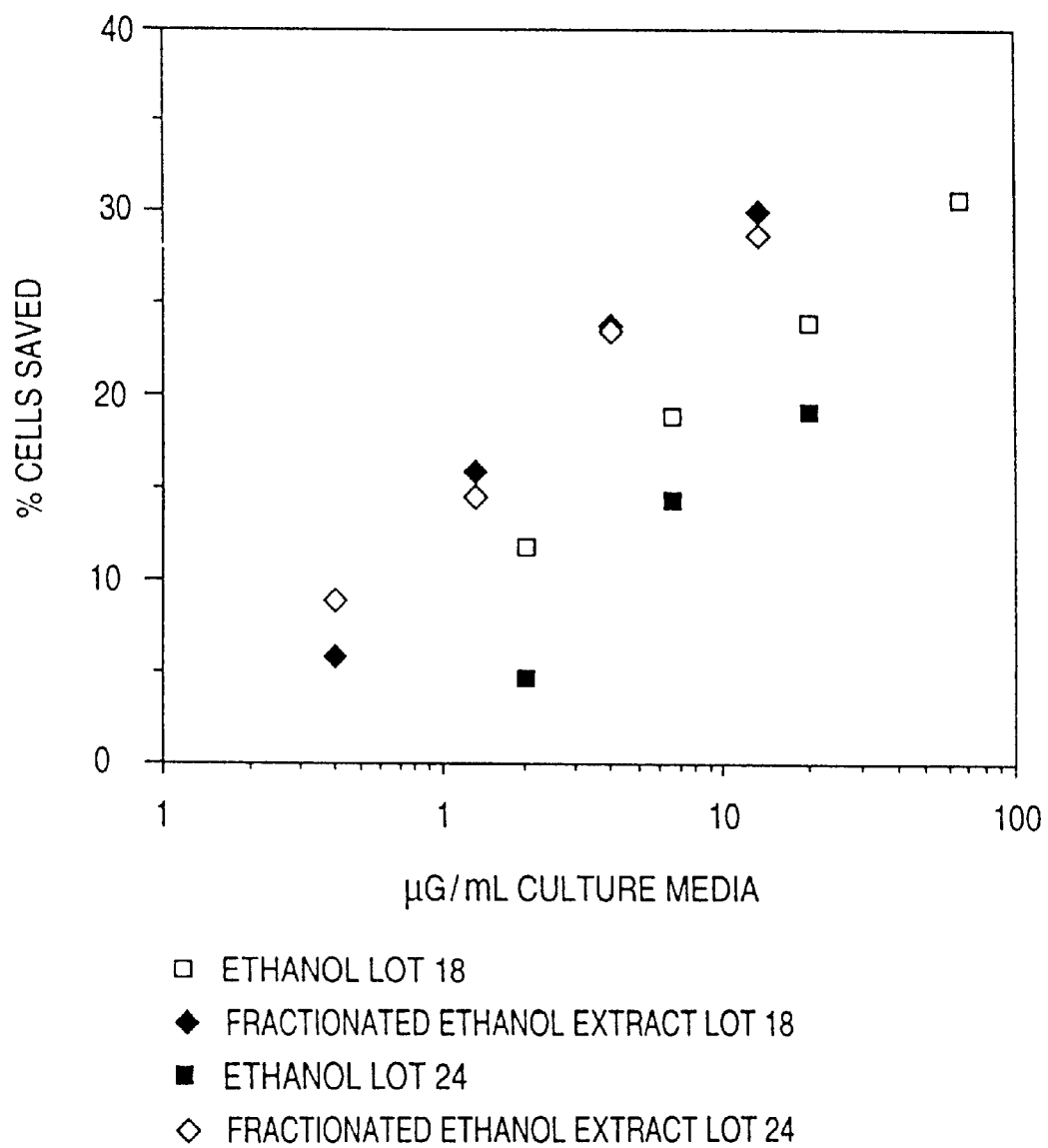
FIG. 2 presents the concentration-dependent anti-apoptotic effect of PAIs on C3H 10T½ cells in exponential growth phase.

In FIG. 2, the results are presented as a percentage of adherent cells in the samples treated with PAIs normalized for the number of adherent cells in the serum free control sample without PAIs. In other words, the percentage of cells saved from apoptosis by treatment with PAIs. The data presented in FIG. 2 demonstrate that soy PAIs have a concentration-dependent anti-apoptotic effect on C3H 10T½ cells in exponential growth phase.

Figure 3:
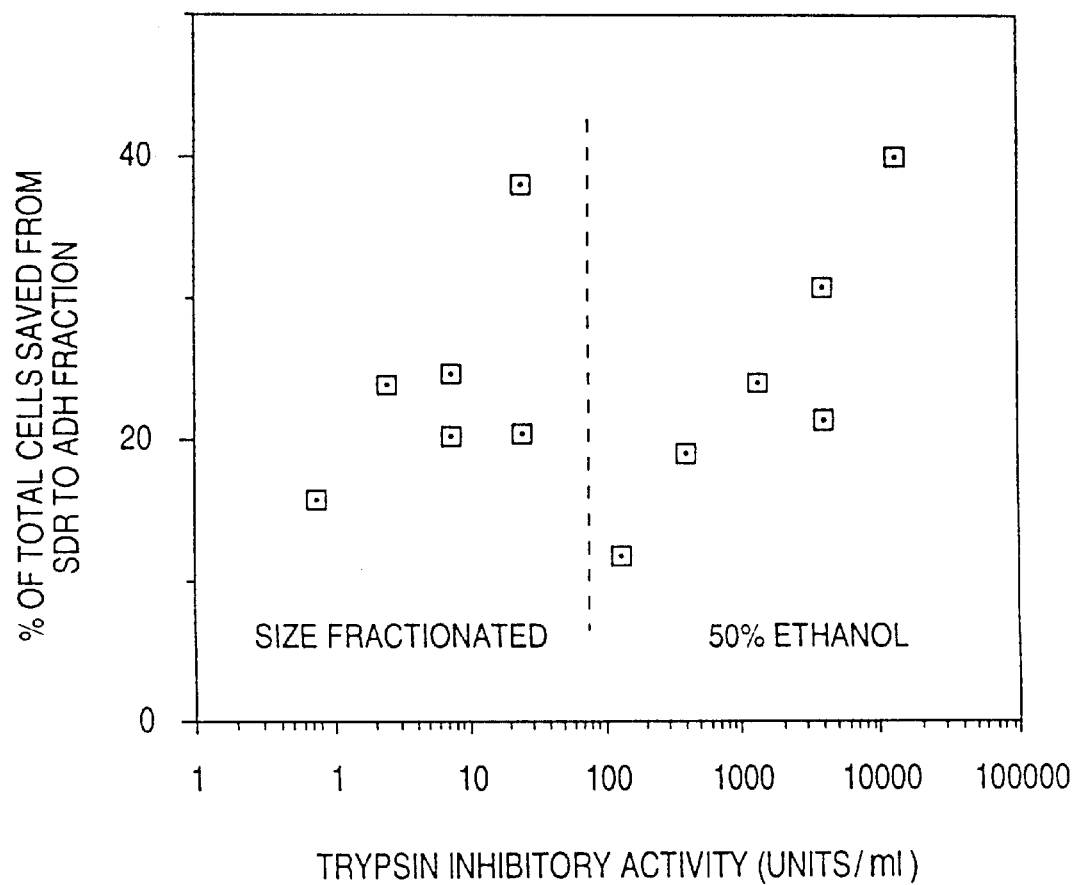
FIG. 3 presents a comparison of the anti-apoptotic activity of PAIs purified by ethanol extraction and PAIs further purified by size exclusion gel filtration chromatography on C3H 10T½ cells. The data are presented as a function of trypsin inhibitory activity.
Figure 4:
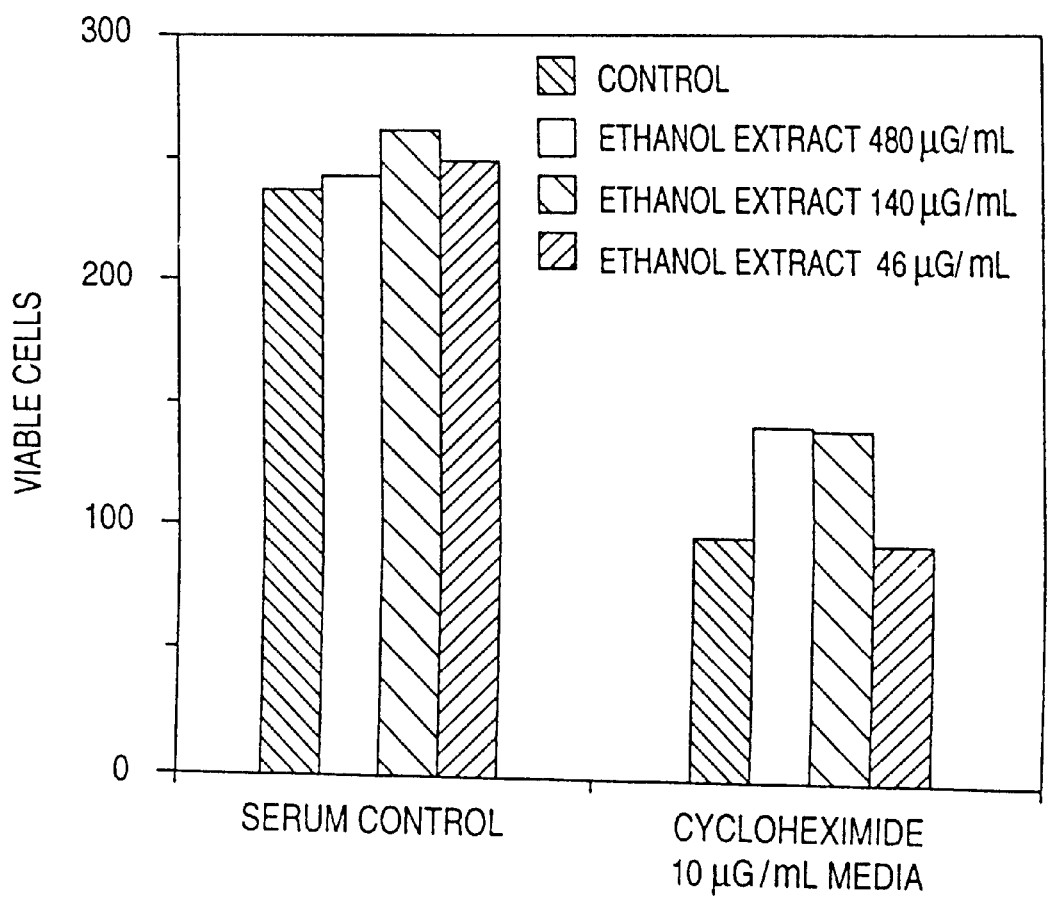
FIG. 4 presents the anti-apoptotic activity of various concentrations of soy PAIs on quiescent C3H 10T½ cells treated with cycloheximide.

In FIG. 3, the anti-apoptotic activity for PAIs after extraction with 50% ethanol (right side) and PAIs which have been further purified by size exclusion gel filtration chromatography (left side) is presented. The results in FIG. 3 are expressed as the percentage of cells saved from apoptosis (SDR cells converted to ADH cells) by treatment with PAIs as compared with the no PAI serum free control samples, all of which is expressed as a function of trypsin inhibitory units. The data presented in FIG. 3 demonstrate that when the concentration of Bowman-Birk inhibitors (as measured by trypsin inhibition) is reduced by size exclusion gel filtration chromatography, the anti-apoptotic activity of PAIs is maintained. Thus, the anti-apoptotic activity of the PAI preparations is not due to the presence of Bowman-Birk inhibitors.

In FIG. 4, the anti-apoptotic activity of various concentrations of soy PAIs on quiescent C3H 10T½ cells treated with cycloheximide is presented. Quiescent cells are those which no longer respond to serum deprivation by entering apoptosis. Rather, apoptosis is stimulated in these cells by the addition of 10 µg/ml cycloheximide in C3H 10T½. Typically, these cells become confluent after about one week in culture and quiescent after about two weeks in culture. The results in FIG. 4 are expressed as viable cells remaining (ADH) after a given treatment. The data in FIG. 4 demonstrate that soy PAIs have a small, but significant anti-apoptotic effect on quiescent C3H 10T½ cells.

EXAMPLE 3

Apoptosis Assay with Neonatal Rat Cardiac Myocytes

Myocytes were prepared from hearts of day-old rats as described in *Circulation Research* 56:884–894, 1985. In brief, the individual cells were obtained by brief, alternating cycles of room temperature trypsinization and mechanical disaggregation. The cells were collected, washed, and resuspended in MEM, 5% fetal bovine serum and 50 U/ml penicillin-G. To reduce contamination by non-myocytes, the cells were pre-plated for 30 minutes. The non-adherent cardiac myocytes were removed from the culture dish, counted on a hemocytometer, and resuspended in medium to a concentration of 600,000 viable cells/ml. The cell suspension was distributed into different culture dishes and incubated in a 37° C., 5% $CO_2$ incubator for 16–24 hours. The yield was 3–5×$10^6$ cells/heart and viable cells were >90% by trypan blue staining.

On the first day of culture, the cells were rinsed with Minimal Eagle Medium (MEN) several times to remove debris and non-adherent cells. They were replenished with serum supplemented media as above. The myocytes were challenged with different conditions in RPMI 1640 medium the next day. The results obtained are presented in Table 2, where PAI 1 x represents the material obtained from 0.1 g of soy flour starting material.

TABLE 2

|  | Neonatal Cardiomyocytes | |
| --- | --- | --- |
|  | Beating Rate | Cell Number |
| Serum-free | + | 11606 |
| Conditioned Media | +++++ | 5128 |
| PAI 1 x | +++ | 15062 |

The results obtained indicate that the PAI fraction is capable of preserving the well-being of cells in the presence of an apoptosis-inducing insult.

EXAMPLE 4

Determination of Carbohydrate Composition of PAI

Figure 5:
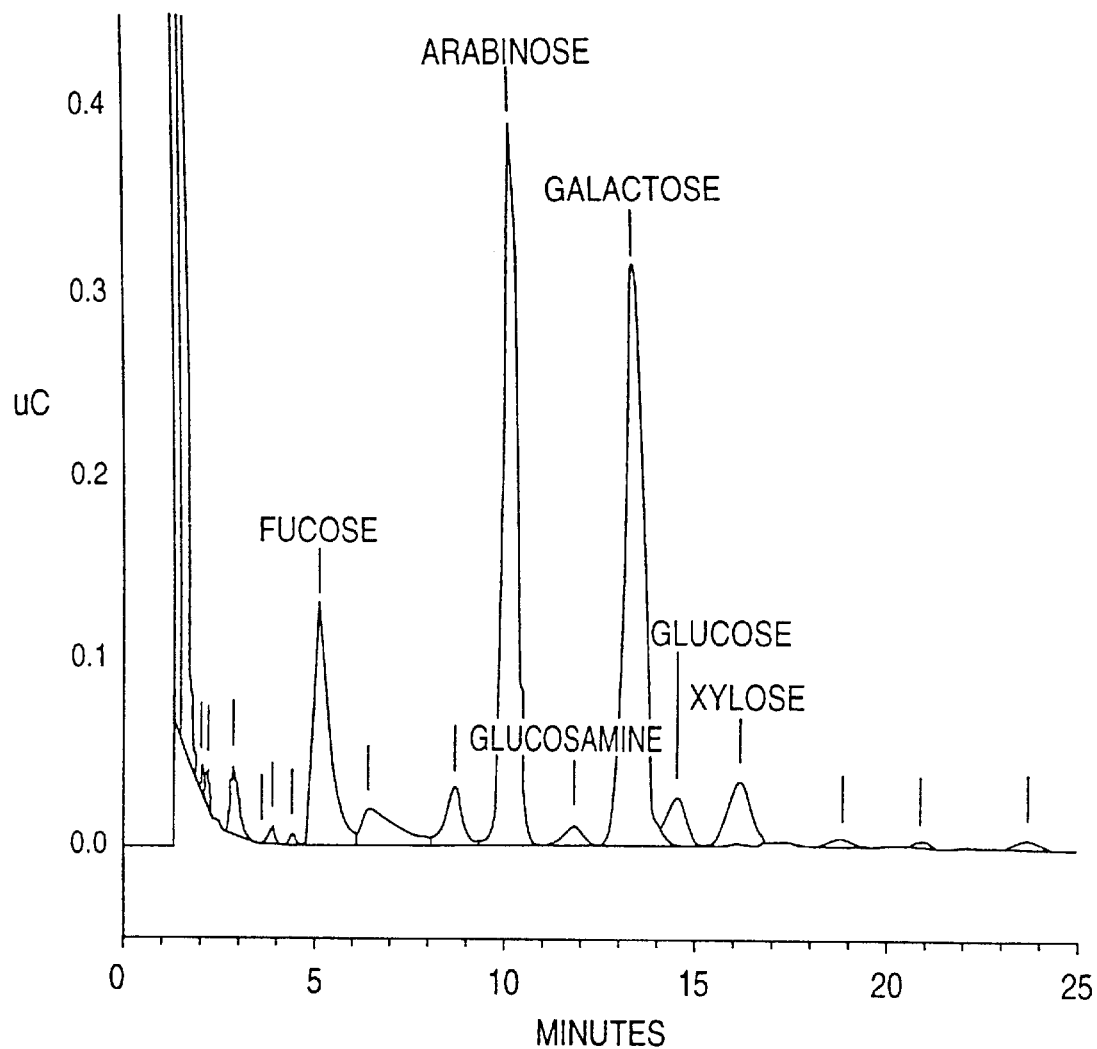
FIG. 5 presents a chromatogram of monosaccharides present in PAI.
Figure 6:
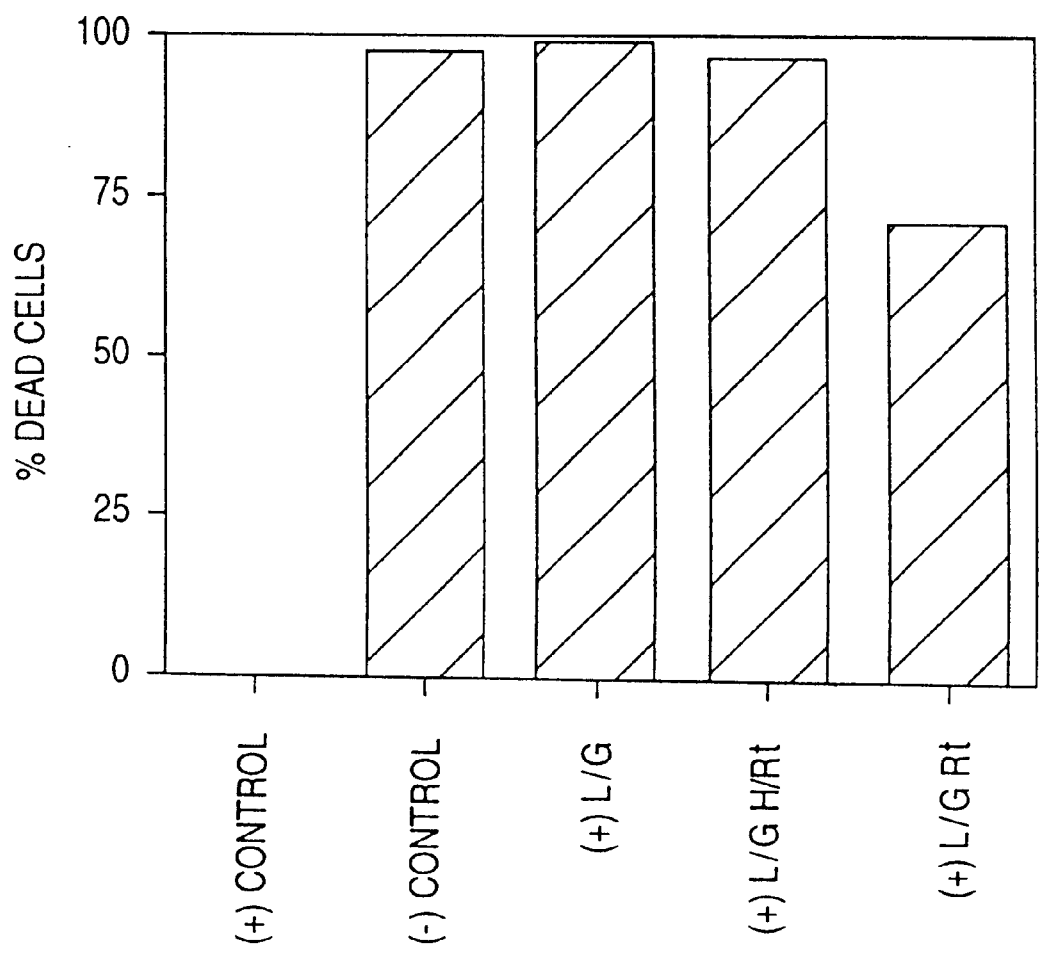
FIG. 6 depicts the results obtained in the rat cardiac myocytes.

In order to determine whether PAIs contain carbohydrate, the L/G fraction of PAIs were exposed to various conditions and the resulting carbohydrate residues were assayed. The PAIs were obtained from Sigma Soy flour Lot No. 103H0820 treated to obtain PAIs as described in Example 1. The free monosaccharides in untreated PAIs were determined by HPLC on Dionex Carbopac™ PA1 in 16 mM NaOH according to the method described in Dionex Document No. 034441. The results obtained are presented in Table 3. The sample was then hydrolyzed with 2N TFA for four hours at 100° C. as described by Hardy and Townsend (1994) Meth. Enzymol. 230:208–225. The results obtained are presented in Table 4. The sample was further hydrolyzed with 6 N HCl for 6 hours at 100° C. as determined by the method described by Hardy and Townsend (1994). The results obtained are depicted in FIG. 5.

TABLE 3

Monosaccharides Detected in PAI

| Monosaccharide | ng/25 µg PAI | ng/mg PAI |
| --- | --- | --- |
| Arabinose | 1.098 | 45.9 |
| Glucose | 0.058 | 2.36 |
| TOTAL | 1.157 | 48.26 |

TABLE 4

Nonosaccharides Released on Hydrolysis

| Monosaccharide | ng/50 µg PAI | µg/mg PAI |
| --- | --- | --- |
| Fucose | 1625 | 32.50 |
| Arabinose | 4605 | 92.10 |
| Galactosamine | 86 | 1.71 |
| Glucosamine | 478 | 9.56 |
| Galactose | 5280 | 105.60 |
| Glucose | 352 | 7.04 |
| Xylose | 520 | 10.40 |
| TOTAL | 12946 | 258.91 |

EXAMPLE 5

Use of PAIs to Prevent Chemotherapy Induced Gastrointestinal Disorders

In order to determine the in vivo activity of the PAIs, the following animal experiments were performed. In Examples 6 and 7 the animal tests were performed essentially as described in Funk and Baker (1991) J. Nutr. 121:1684–1692; and Funk and Baker (1991) J. Nutr. 121:1673–1683. Briefly, male Sprague-Dawley rats were used to determine if isolated AcE and L/G obtained from sly flour as described in Example 1 could alleviate methotrexate (MTX) toxicity. The rats were housed in individual, wire-bottom stainless steel cages and were adapted to their respective diets for 7 days prior to injection of MTX and remained on the same diets for 7 days after injection. Diets fed were semipurified rat food with the following additions:
1. casein
2. casein and soy concentrate (10 g and 10 g)
3. casein and soy flour (10 g and 10 g)
4. casein and AcE
5. casein and L/G AcE and L/G were used at concentrations equal to that extracted from the soy starting material.

Records of rat weight and food intake were kept during the preinjection period. Rats were injected IP with 20 mg/kg MTX. During the 7 day postinjection period, rat weight, food intake and incidence of diarrhea were recorded. Rat weight and food intake data were analyzed using the nonparametric Kruskal-Wallis test and post-hoc comparison. The P value was adjusted for multiple comparisons by dividing 0.05 by the number of comparisons made (10). A nonparametric test was used because variances between groups were not homogeneous and thus assumptions for analysis of variances were not met. Food intake following MTX injection was expressed as a percentage of the average intake 3 days prior to injection for each animal. Thus, each animal served as its own control. Only days 3, 4, 5, and 6 post MTX injection were analyzed statistically. The reason for this is that days 3 and 4 are when toxicity is most severe and days 5 and 6 are when recovery begins. Diarrhea data were analyzed using both the Fisher's Exact Test and loglinear analysis.

Figure 7:
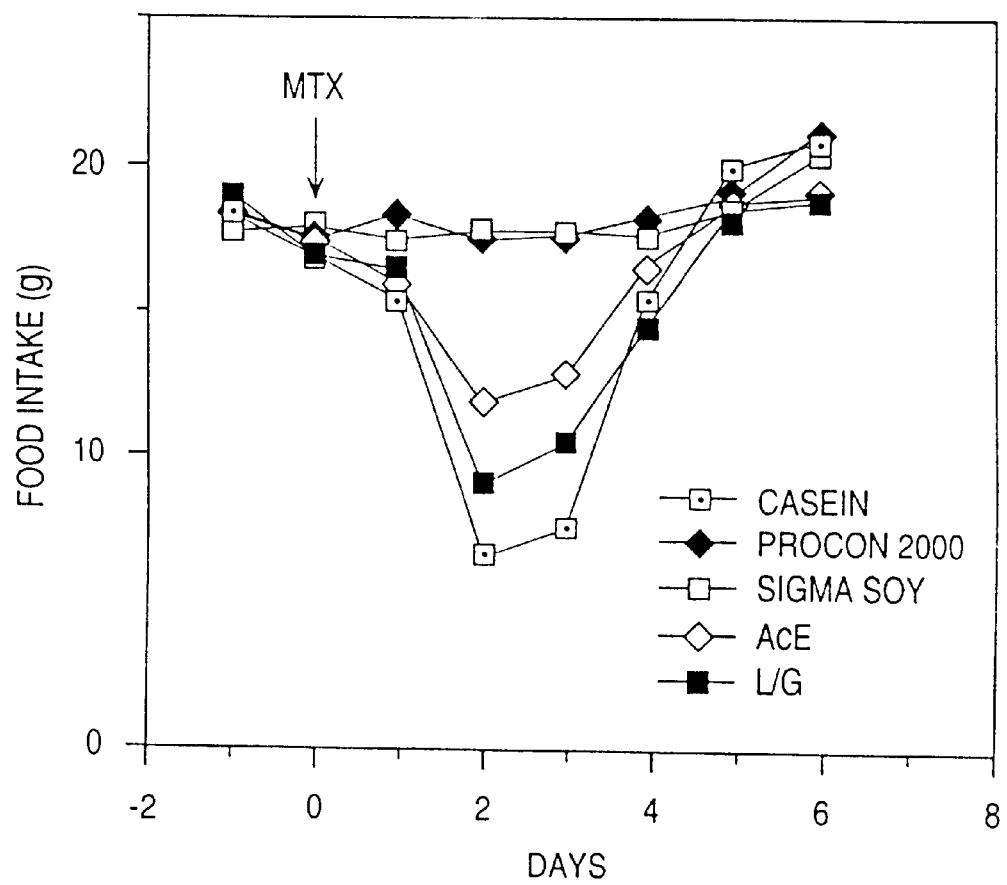
FIG. 7 is a graph depicting the effect of soy flour extracts on methotrexate treated rats.

Results showed that soy concentrate and soy flour starting material as well as both the AcE and L/G were capable of improving food intake following MTX injection (Table 5 and FIG. 7). On day 3 food intake for rats consuming soy flour and soy concentrate was statistically greater than for those consuming casein alone or casein with L/G. Rats consuming casein with AcE were intermediate in food intake on day 3 and statistically similar to all groups except those consuming soy flour. Day 4 showed an identical pattern except since food intake for rats consuming L/G rose slightly as compared with day 3, these rats were no longer statistically different from rats consuming soy concentrate although numerically food intake remained substantially lower. Recovery was evident on days 5 and 6 and food intake was statistically similar among all groups. Weight change (Table 6) reflected patterns observed in food intake which is expected. Rats consuming soy concentrate and soy flour gained a substantial amount of weight during the first 4 days following MTX injection. Rats consuming AcE, L/G or casein alone gained less weight and those consuming casein gained statistically less than those fed soy concentrate or soy flour. Differences in incidence of diarrhea were not statistically different but the pattern of diarrhea was consistent with food intake and weight change (Table 6). Rats consuming soy concentrate or soy flour had no diarrhea while a slight amount of diarrhea was present in rats consuming AcE (10%) and a moderate amount of diarrhea was present in those consuming L/G or casein alone (30–40%).

In conclusion, this experiment showed that soy concentrate and soy flour offered the best protection of the components tested. Casein with AcE appeared to be intermediate and superior to casein alone or L/G as evidenced by better maintenance of food intake and weight and lower incidence of diarrhea. This result indicates that compounds isolated from soy can provide protection against MTX toxicity. In this experiment, the L/G fraction at this concentration did not appear to provide protection. However, Example 7 shows that increased concentrations of L/G are effective.

EXAMPLE 6

Use of PAIs to Prevent Chemotherapy Induced Gastrointestinal Disorders

Male Sprague-Dawley rats were used to determine if graded levels of isolated soy fractions (AcE, L/G and MAcE) could alleviate methotrexate (MTX) toxicity. Animals were housed in individual, wire-bottom stainless steel cages. Rats were adapted to their respective diets for 7 days prior to injection of MTX and remained on the same diets for 7 days after injection. Diets fed were semipurified and casein with additions as follows:
1. No additions
2. AcE (100 mg/20 g casein; 1×)
3. AcE (300 mg/20 g casein; 3×)
4. AcE (1000 mg/20 g casein; 10×)
5. L/G (10 mg/20 g casein; 1×)
6. L/G (30 mg/20 g casein; 3×)
7. L/G (100 mg/20 g casein; 10×)
8. MAcE (100 mg/20 g casein; 1×)
9. MAcE (300 mg/20 g casein; 3×)
10. MAcE (1000 mg/20 g casein; 10×)
11. MAcE (3000 mg/20 g casein; 30×)

Note that MAcE is soy molasses extracted as for soy flour to obtain AcE. Each diet group contained 8 rats except for the group receiving casein with no added compound which

TABLE 5

Effect of Diet and Methotrexate on Food Intake[1]

| Diet | Pretreatment Food Intake[2] (g/day) | Food Intake Posttreatment (%)[3] | | | |
|---|---|---|---|---|---|
| | | day 3 | day 4 | day 5 | day 6 |
| Casein | 18.4 ± 0.6 | 34.1 ± 11.0$^a$ | 39.6 ± 13.0$^a$ | 83.0 ± 12.5 | 108.9 ± 2.7 |
| Soy Concentrate-Casein (50/50) | 18.4 ± 0.5 | 94.3 ± 6.5$^{bc}$ | 94.8 ± 5.1$^{bc}$ | 98.9 ± 2.5 | 101.8 ± 3.3 |
| Soy Flour-Casein (50/50) | 17.8 ± 0.4 | 99.0 ± 4.6$^c$ | 99.1 ± 2.0$^c$ | 98.2 ± 2.3 | 102.1 ± 3.5 |
| Casein-AcE | 18.5 ± 0.4 | 63.6 ± 9.3$^{ab}$ | 68.3 ± 10.3$^{ab}$ | 88.6 ± 6.9 | 99.5 ± 4.0 |
| Casein-L/G | 19.0 ± 0.8 | 46.3 ± 11.7$^a$ | 53.9 ± 14.2$^{ab}$ | 75.3 ± 13.1 | 96.4 ± 11.0 |

[1]Values are means ± standard error of the mean for ten male rats. Methotrexate was injected IP following a 7-day adaptation period. Values in columns with unlike superscripts differ (P ≤ 0.05, Kruskal-Wallis test and post hoc comparison).
[2]Pretreatment food intake represents the mean of the 3 day period prior to the administration of MTX.
[3]Posttreatment intake represents the % of pretreatment intake.

TABLE 6

Effect of Diet and Methotrexate on Rat Weight[1]

| Diet | Average Pretreatment Weight[2] (g) | Weight Change | | Incidence of Diarrhea (%) |
|---|---|---|---|---|
| | | day 0–4 (g) | day 4–6 (g) | |
| Casein | 230.0 ± 4.7 | 1.2 ± 5.3$^a$ | 16.3 ± 1.5 | 30 |
| Soy Concentrate-Casein (50/50) | 227.2 ± 4.7 | 22.1 ± 1.5$^b$ | 9.7 ± 1.6 | 0 |
| Soy Flour-Casein (50/50) | 227.2 ± 4.4 | 22.7 ± 1.6$^b$ | 10.1 ± 1.0 | 0 |
| Casein-AcE | 230.3 ± 3.2 | 11.7 ± 4.1$^{ab}$ | 13.5 ± 2.1 | 10 |
| Casein-L/G | 232.9 ± 5.1 | 6.9 ± 5.6$^{ab}$ | 9.8 ± 4.5 | 40 |

Figure 8:
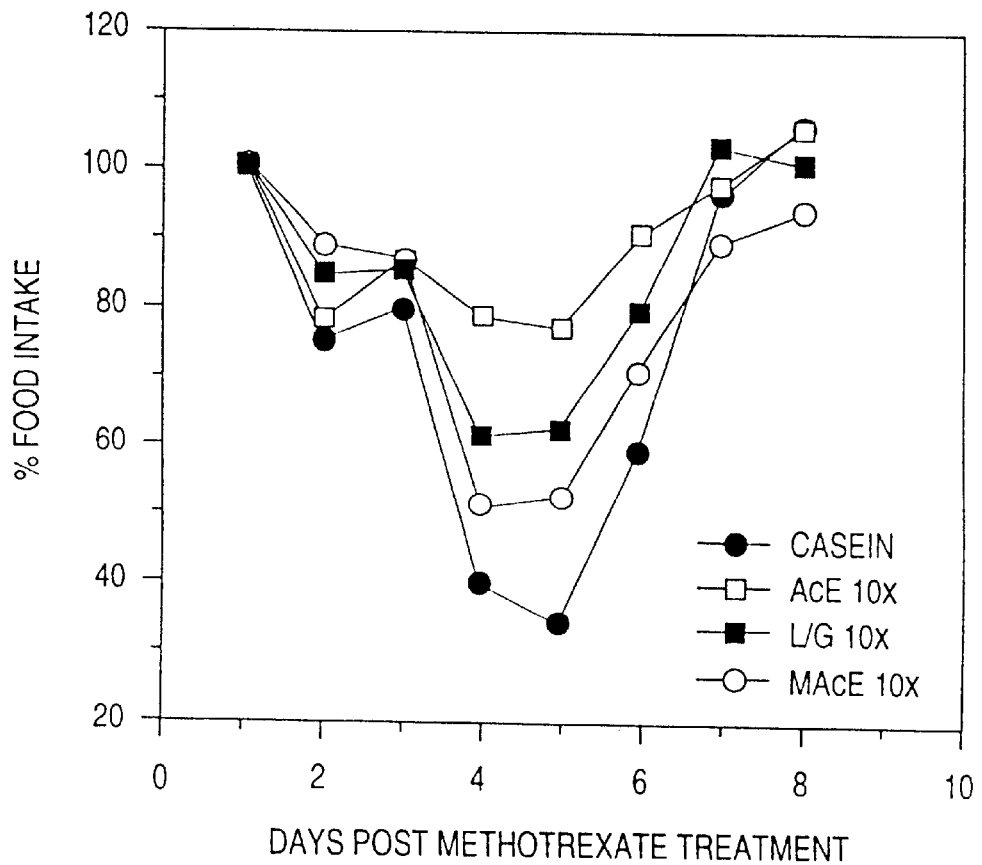
FIG. 8 is a graph depicting the effect of soy flour extracts on methotrexate treated rats.
Figure 9:
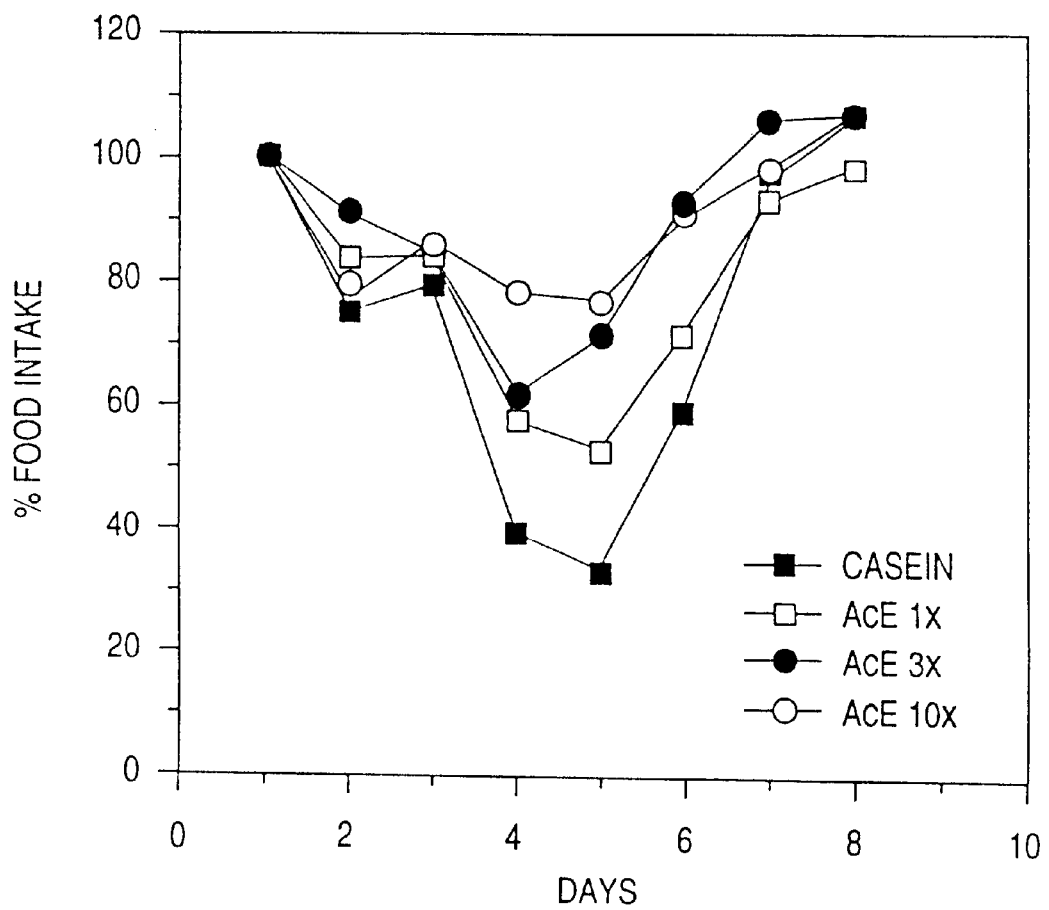
FIG. 9 is a graph depicting the effect of soy AcE on methotrexate treated rats.
Figure 10:
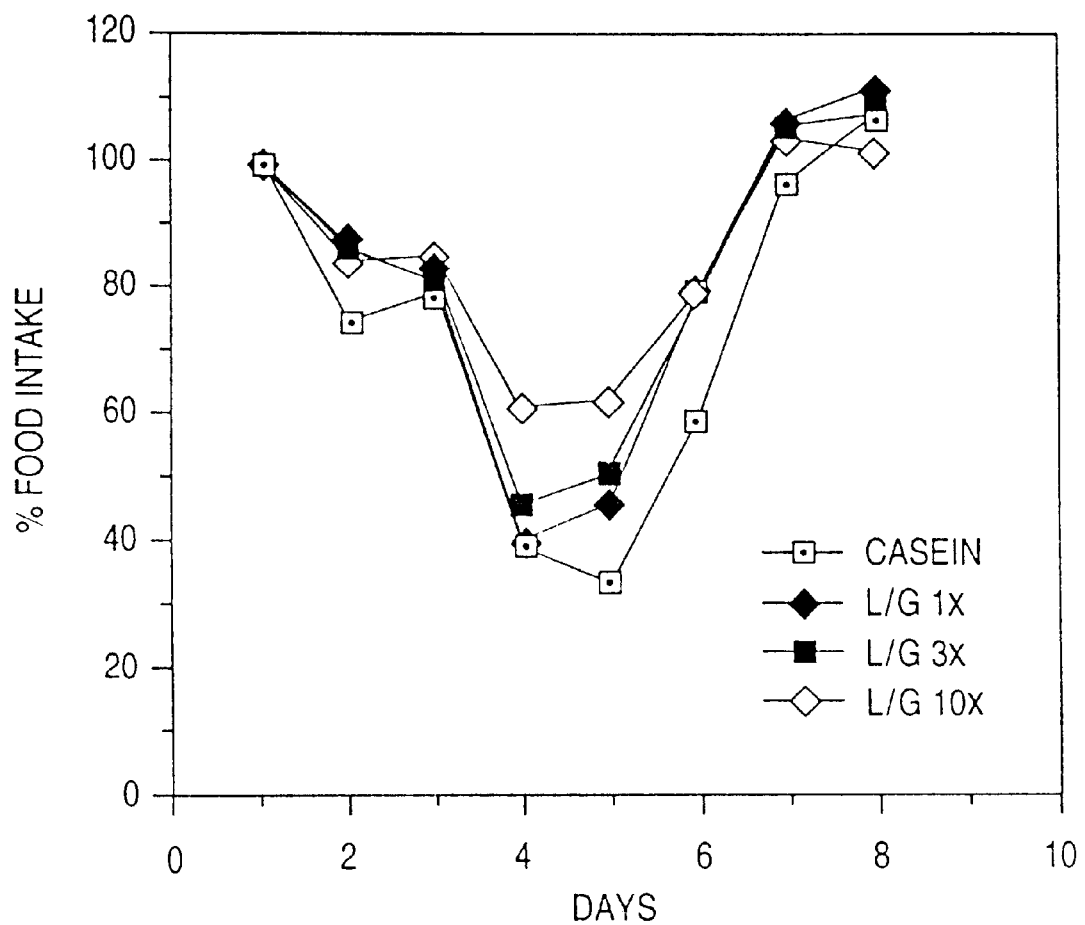
FIG. 10 is a graph depicting the effect of soy flour extracts on methotrexate treated rats.
Figure 11:
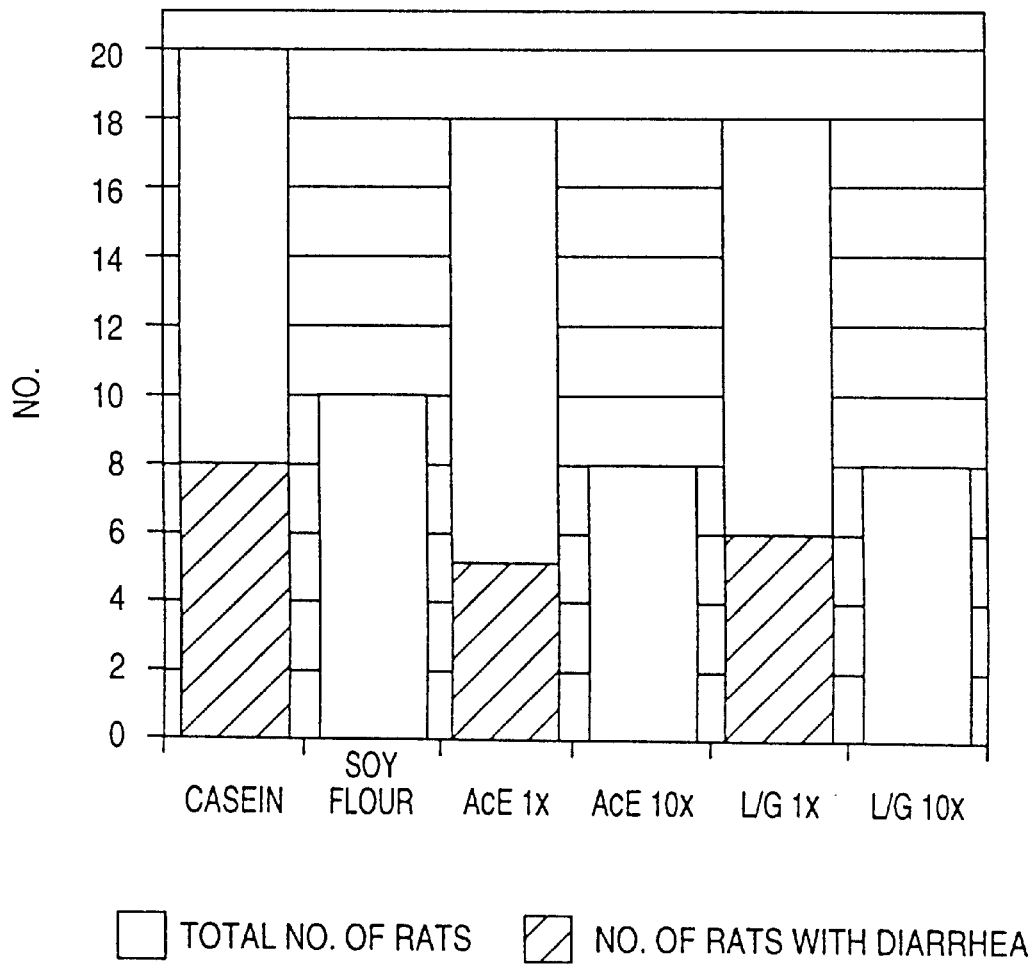
FIG. 11 is a bar graph depicting the incidence of rats presenting with diarrhea after treatment with methotrexate and various diets.
Figure 12:
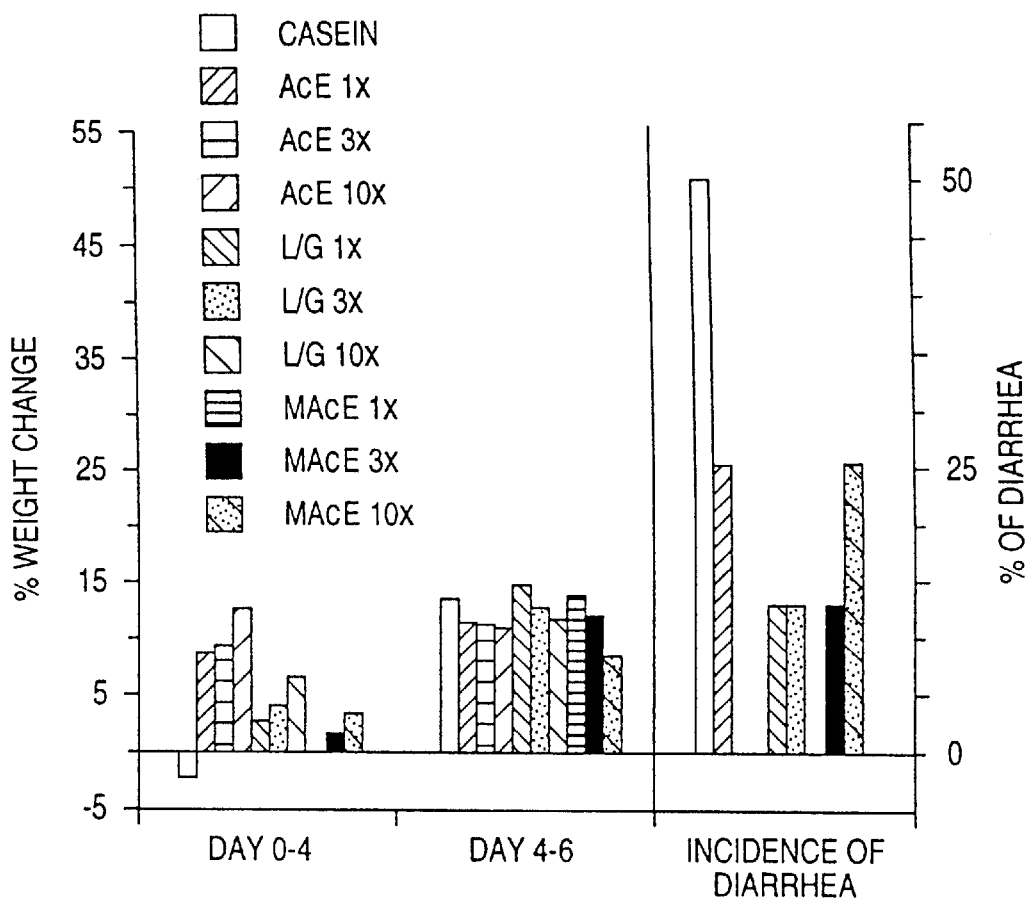
FIG. 12 is a bar graph summarizing the incidence of diarrhea and weight gain in rats treated with methotrexate and various diets.

[1]Values are means ± standard error of the mean for ten male rats. Methotrexate was injected IP following a 7-day adaptation period. Values in columns with unlike superscripts differ (P ≤ 0.05, Kruskal-Wallis test and post hoc comparison).
[2]Pretreatment weight indicates the average weight on the day of injection.

contained 10 rats. Records of rat weight and food intake were kept during the preinjection period. Rats were injected IP with 20 mg/kg MTX. During the 7 day postinjection period, rat weight, food intake and incidence of diarrhea were recorded. Food intake for various groups is depicted in FIGS. 8–10. Incidence of diarrhea is depicted in FIG. 11. Rat food intake for the entire group is depicted in FIG. 12. Rat weight and food intake data were analyzed by ANOVA using a factorial arrangement of treatments to test the main effects of compound and dose and the possible interaction between compound and dose. Factorial analysis was done using only the treatment groups with the 1×, 3× and 10× doses of each of the compounds. In addition t-tests were used to determine differences between the 10× level of each compound and the diet containing only casein. Food intake following MTX injection was expressed as a percentage of the average intake 3 days prior to injection for each animal. Thus, each animal served as its own control. Only days 3, 4, 5 and 6 post MTX injection were analyzed statistically. The reason for this is that days 3 and 4 are when toxicity is most severe and days 5 and 6 are when recovery begins. Diarrhea data were analyzed using Fisher's Exact Test. Only the 10× levels for each of the compounds were analyzed statistically against casein for differences in diarrhea incidence. FIG. 12. The reason for this is that Fisher's test is a conservative test. When multiple comparisons are done the error rate must be adjusted. In order to increase the chances of statistical significance, only those comparisons were done where the best response for each of the compounds had been realized as evidenced by food intake and weight change data.

Results of the factorial analysis of food intake and weight change are presented in Tables 7 and 8. The results showed that the AcE compound was the most effective at alleviating MTX toxicity. Food intake was greater for all AcE groups combined than for both of the other groups on day 3 following MTX dosing and remained greater than those consuming MAcE on day 4 (P<0.05). Decreased toxicity in rats consuming AcE as compared with MAcE was also reflected in weight patterns as those consuming AcE gained more weight during the first four days postdosing than those consuming MAcE (P<0.05). Improvements in intake and maintenance of weight were seen with increasing levels of each of the compounds with the exception of the 30× level of MAcE, although this was not statistically significant. The level of each compound where response was the best was 10×. In comparing the 10× level of each of the compounds against casein alone, AcE was statistically greater on days 3, 4 and 5 postdosing (P<0.05). The pattern of diarrhea was consistent with the food intake results. Fifty percent of the animals consuming casein developed diarrhea. No animals consuming the 10× level of the compounds developed diarrhea which was statistically less than those consuming casein alone (P=0.088). All other groups experienced some diarrhea with the exception of those consuming the 3× level of AcE.

In conclusion, for the compounds tested, AcE was the best at alleviating MTX toxicity. L/G and MAcE positively affected MTX toxicity as evidenced by decreased incidence of diarrhea as compared with casein alone and statistically nonsignificant improvement in food intake and weight maintenance. It is possible that higher levels of AcE and L/G may provide additional protection. The 30× level of MAcE proved to be ineffective and closely resembled casein alone. Therefore, it appears that once a threshold is reached higher levels are detrimental. It is possible that MAcE may be more effective at a dose somewhere between the 10× and 30× levels tested in this experiment.

TABLE 7

Effect of Diet and Methotrexate on Food Intake[1]

| Diet | n | Pretreatment Food Intake (g/day) | Food Intake Posttreatment (%) | | | |
|---|---|---|---|---|---|---|
| | | | day 3[2,3] | day 4[3,4] | day 5[3] | day 6 |
| 1. | 10 | 18.5 ± 0.5 | 39.5 ± 11.5 | 33.5 ± 11.7 | 58.9 ± 12.4 | 96.3 ± 5.9 |
| 2. | 8 | 19.7 ± 0.6 | 57.6 ± 12.8 | 52.7 ± 16.6 | 71.5 ± 11.2 | 93.0 ± 4.8 |
| 3. | 8 | 16.2 ± 0.4 | 61.4 ± 7.0 | 71.3 ± 11.3 | 92.6 ± 6.0 | 105.6 ± 4.7 |
| 4. | 8 | 16.7 ± 0.4 | 78.2 ± 9.2 | 76.7 ± 11.0 | 90.3 ± 6.7 | 97.8 ± 4.3 |
| 5. | 8 | 17.9 ± 0.4 | 40.0 ± 8.4 | 45.9 ± 11.4 | 80.3 ± 11.4 | 105.7 ± 3.6 |
| 6. | 8 | 18.3 ± 0.7 | 46.0 ± 9.8 | 50.7 ± 12.8 | 79.6 ± 12.0 | 105.2 ± 5.3 |
| 7. | 8 | 17.3 ± 0.6 | 60.8 ± 9.9 | 61.9 ± 12.8 | 79.2 ± 11.8 | 103.3 ± 3.9 |
| 8. | 8 | 18.5 ± 0.7 | 40.8 ± 10.2 | 34.5 ± 9.4 | 59.1 ± 9.8 | 100.2 ± 4.8 |
| 9. | 8 | 17.2 ± 0.5 | 38.0 ± 8.4 | 45.4 ± 10.6 | 82.2 ± 11.7 | 100.4 ± 6.4 |
| 10. | 8 | 16.9 ± 0.4 | 50.4 ± 5.8 | 52.2 ± 9.4 | 70.4 ± 13.9 | 89.3 ± 12.0 |
| 11. | 8 | 16.4 ± 0.4 | 30.0 ± 6.0 | 33.9 ± 9.8 | 58.1 ± 9.1 | 110.4 ± 4.0 |

Footnotes:
[1]Values are means ± standard error of the mean for male rats. Methotrexate was injected IP following a 7-day adaptation period. Pretreatment food intake represents the mean of the 3-day period prior to the administration of methotrexate. Posttreatment intake represents the % of pretreatment intake.
[2]The casein-AcE groups (2–4) maintained a better posttreatment intake than casein-L/G (5–6) and casein-MAcE (8/11) groups (P < 0.05, ANOVA and Student Newmans-Keuls tests following factorial analysis).
[3]Casein-AcE (10×) (3) animals had a greater posttreatment intake than casein (P < 0.05), t-test).
[4]The casein-AcE groups maintained a better posttreatment intake than the casein-MAcE groups (P < 0.05, ANOVA and Student Newmans-Keuls tests following factorial analysis).

TABLE 8

Effect of Diet and Methotrexate on Rat Weight and Diarrhea[1]

| Diet | n | Average Pretreatment Weight (g) | Weight Change day 0–4[2] (g) | Weight Change day 4–6 (g) | Incidence of Diarrhea[3] (%) |
|---|---|---|---|---|---|
| 1. | 10 | 220.2 ± 5.5 | −2.1 ± 1.8 | 13.2 ± 1.8 | 50 |
| 2. | 8 | 233.5 ± 4.2 | 8.3 ± 5.6 | 11.1 ± 0.7 | 25 |
| 3. | 8 | 224.7 ± 3.6 | 9.0 ± 3.0 | 10.8 ± 2.0 | 0 |
| 4. | 8 | 227.3 ± 3.8 | 12.4 ± 5.4 | 10.6 ± 1.5 | 0 |
| 5. | 8 | 232.6 ± 2.7 | 2.5 ± 3.6 | 14.3 ± 1.9 | 12.5 |
| 6. | 8 | 225.5 ± 3.3 | 3.8 ± 3.9 | 12.2 ± 1.8 | 12.5 |
| 7. | 8 | 232.6 ± 4.5 | 6.3 ± 5.0 | 11.3 ± 1.2 | 0 |
| 8. | 8 | 234.1 ± 6.3 | 0.0 ± 2.3 | 13.5 ± 2.4 | 12.5 |
| 9. | 8 | 226.1 ± 3.2 | 1.5 ± 4.9 | 11.6 ± 1.7 | 25 |
| 10. | 8 | 235.2 ± 2.3 | 3.1 ± 3.2 | 7.9 ± 3.8 | 0 |
| 11. | 8 | 220.6 ± 2.8 | −2.3 ± 3.4 | 140.0 ± 1.2 | 25 |

Footnotes:
[1]Values are means ± standard error of the mean for male rats. Methotrexate was injected IP following a 7-day adaptation period. Pretreatment weight indicates the average weight on the day of injection.
[2]The casein-AcE groups (2–4) maintained overall weight better during acute toxicity than the casein-MAcE groups (8–11) ($P < 0.05$, ANOVA and Student Newmans-Keuls tests following factorial analysis). Casein-AcE (10x) (4) animals showed significantly less weight loss than casein ($P < 0.05$), t-test).
[3]Animals consuming the 10x level of the compounds (4, 7, 10) had a significantly lower incidence of diarrhea than animals consuming casein ($P < 0.088$, Fisher's exact test for diarrhea).

EXAMPLE 7

Use of PAIs to Inhibit Apoptosis in Lymphocytes Obtained from an HIV-infected Patient The L/G fraction of PAIs isolated from soy flour was tested for its ability to inhibit apoptosis in lymphocytes from an HIV-infected patient.

Peripheral blood monocytes (PBMCs) were obtained from the patient and isolated according to standard methods. The PBMCs were cultured at $2\times10^6$/well in 24-well plates (Costar×Cambridge, Mass.) for 72 hours at 37 C. and 5% $CO_2$ containing 2 ml/well of RPMI 1640 with antibiotics and 10% hAB. Some cultures contained 10 μg/ml Pokeweed Mitogen (PWM) (Sigma, St. Louis, Mo.). Suspensions of thymocytes were used immediately after removal or after culture in RPMI+10% fetal bovine serum with 5 μM dexamethasone (DEX) (Sigma—St. Louis, Mo.) for 18 hours. The cells were exposed for three days to the L/G fractions at the concentrations indicated below where 0.5 gEQ is the fraction derived from 0.5 g starting weight of flour.

| Lane # | PWM | L/G |
|---|---|---|
| 1 | − | None |
| 2 | − | Purified L/G - 0.5 gEQ/ml |
| 3 | − | Purified L/G - 0.05 gEQ/ml |
| 4 | − | Purified L/G - 0.005 gEQ/ml |
| 5 | + | None |
| 6 | + | Purified L/G - 0.5 gEQ/ml |
| 7 | + | Purified L/G - 0.05 gEQ/ml |
| 8 | + | Purified L/G - 0.005 gEQ/ml |
| 9 | − | Untreated rat thymocytes (negative control) |
| 10 | − | Dexamethasone-treated rat thymocytes (positive control) |
| 11 | − | 123 bp DNA standards |

DNA was extracted and gel electrophoresis was performed as described by Sambrook et al. Molecular Cloning—Laboratory Manuals, 2nd Ed. Cold Spring Harbor Laboratory Press, NY pp. 134–135, E3–E4 and E10–11. Briefly, cells harvested were pelleted by centrifugation and lysed in 400 μl of 50 mM KCl, 10 mM Tris-HCl (pH 8), 1% NP-40, 1% Tween-20, and 0.5 mg/ml Proteinase K (Boehringer Mannheim, Indianapolis, Ind.) at 60 C. for 1 hour. After extraction with phenol-chloroform and recovery with ethanol, the DNA was run through a 1.5% agarose gel (SeaKem, Rockland, Me.) in 90 mM Tris-Borate, 2.5 mM EDTA, pH 8.3 at 30 to 50 V for approximately 4 hours. A 123 base pair ladder (GIBCO BRL, Gaithersburg, Md.) was used as the DNA standard (DS) markers. Gels were stained with 1 μg/ml ethidium bromide (Molecular Probes, Eugene, Oreg.) and destained in distilled $H_2O$.

Figure 13:
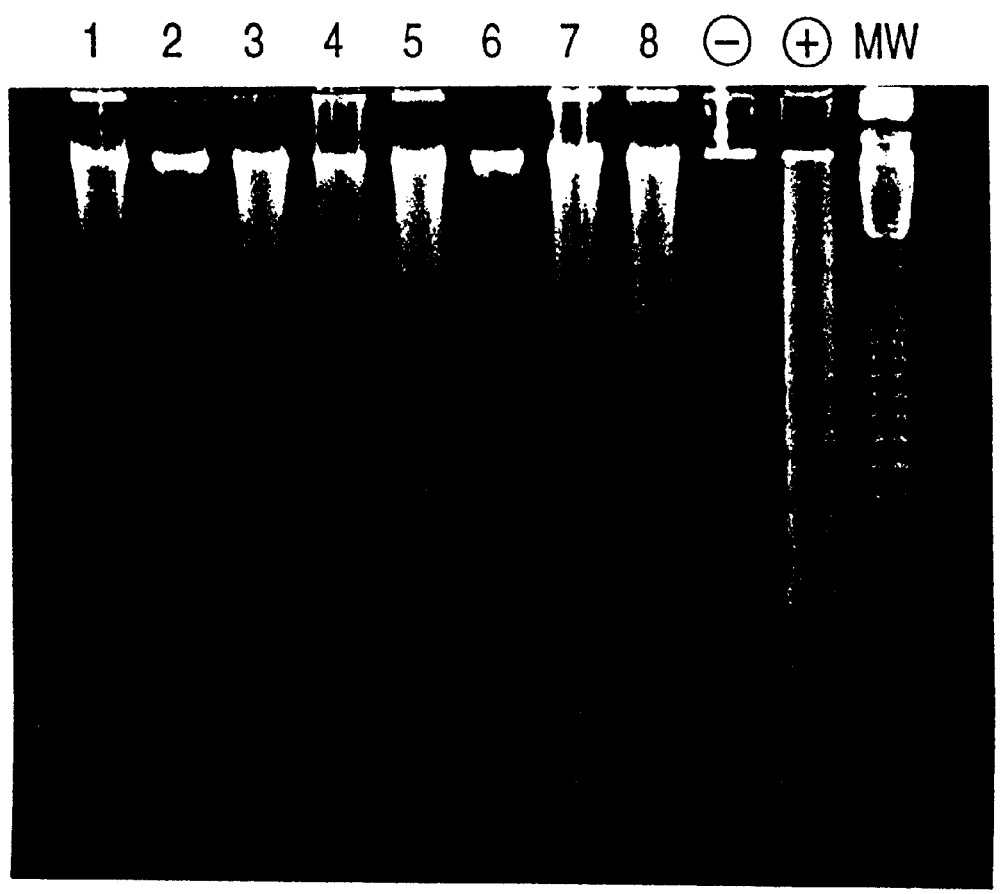
FIG. 13 is a photograph depicting DNA laddering as a measure of apoptosis in lymphocytes obtained from an HIV-infected individual.

The results are shown in FIG. 13 where the lanes are as indicated above.

The results obtained indicate that significant DNA fragmentation was observed in the absence of PWM-stimulation (lane 1) and this fragmentation was almost completely inhibited in cultures that contained 0.5 gEQ of L/G (lane 2). Lower concentrations of L/G (0.05 gEQ and 0.005 gEQ) did not inhibit DNA fragmentation in the absence of PWM (lanes 3 and 4) or in the presence of PWM (lanes 7 and 8). The DNA fragmentation in the presence of PWM (lane 5) was increased in comparison to cultures without PWM (lane 1). A slight inhibition of DNA fragmentation in the presence of PWM was observed in the presence of 0.5 gEQ L/G (lane 6) in comparison to lane 5. Negative and positive controls (lanes 10 and 11) worked as expected.

EXAMPLE 8

Further Purification and Characterization of PAIs

Samples were purified by extraction as described in Example 1 then silica, diol and HPLC silica chromatography were performed and the products analyzed for chemical composition, molecular weight, and structure. From the silica HPLC, the flow through and five major peaks were observed.

The flow through contained lysophosphatidic acid as determined by NMR proton and carbon 13 analysis. Fatty acid analysis indicated a mixture of C16:0 and C18:2 (hexadecanoic and 9,12-octadecadienoic) in the ratio of 60:40 to 50:50 depending on the soy starting material.

Peak two was identified as phosphatidyl inositol by mass spectrometry, NMR, and co-migration with authentic standards on TLC analysis. In addition, fatty acid analysis demonstrated a similar ratio of C16:0 and C18:2 (hexadecanoic and 9,12-octadecadienoic) on each of the two possible positions in the ratio of 60:40 (this is the majority and is typical for soy phosphatidyl inositol) to 50:50 depending on the position of sample in the peak i.e. leading or trailing edge.

Peak three contains four identifiable fatty acids of the C16:0, C18:0 C18:1 and C18:2 varieties i.e., hexadecanoic, octadecanoic, cis-9-octadecenoic, and 9,12-octadecadienoic in the ratio of 40:5:10:45, the most active containing a ratio of 45:5:5:45. In addition, this peak contains an unidentified fatty acid component migrating at an elution time of 16.2 to 16.3 minutes; much later than 16:0 (at 10.8 minutes) and the 18:0, 18:1, and 18:2 that elute between 13.2 and 14.1 minutes. The unidentified moiety comprised from 50 to 68% of the total fatty acid present. Using mass spectrometry analysis, lysophosphatidyl inositol was identified, with both the 16:0 and 18:2 fatty acid varieties. This peak also contains phosphatidyl inositol with 16:0 and 18:2 fatty acid on the R1 and R2 positions. Three unidentified species with molecular weights of 861, 864 and 939–940 were also found.

Peak 3 has been designated "D" in that it has been found primarily in the soy flour extract. Peak 4, designated "B", has no anti-apoptotic activity.

Peak 5 has been designated "L" and is found primarily in the lecithin-derived material. Peak 5 contains two identifiable fatty acids of the C16:0, C18:0 varieties, i.e. hexadecanoic and octadecanoic, in the ratio of 75:25. In addition, this peak contains an unidentified fatty acid component migrating with an elution time of 19 to 22 minutes. The unidentified moiety comprises 66% of the total fatty acid present. Using mass spectrometry, phosphatidyl inositol was identified in the 16:0 and 18:0 fatty acid variety. Two unidentified species with molecular weights of 113 and 191 were also observed.

Fatty acids were analyzed as fatty acid methyl esters. The transesterification reagent was anhydrous HCl/MeOH prepared as described in Christie "HPLC and Lipids" (1987), and analyzed as described in Christie "Gas Chromatography and Lipids: a practical guide" (1989), both published by Oily Press Ltd. Dundee Scotland. To each sample, 300 uL of $CH_2Cl_2$ and 700 uL of HCl/MeOH was added. Derivatization was done under nitrogen at room temperature for 18 hours. After that, 1 mL of water was added and the samples were extracted with 3×2 mL of hexane. The combined extractions were dried under a stream of nitrogen redissolved in 100 uL of hexane and transferred to GC-MS vials. Analyses of samples were performed on a Hewlett-Packard 5890 gas chromatograph with a Hewlett-Packard 5971 series mass selective detector as described in van den Berg et al. (1993) *J. Lipid Res.* 34:2005–2012.

Electrospray mass spectrometry (MS) was performed on a VG BloQ Triple quadrupole mass spectrometer with electrospray ionization in negative mode. The source temperature was 80° C., the solvent was methanol or methanol with 0.05% ammonium acetate at 5 uL/min, and capillary voltage was 4.7 kV. Mass spectrometry is generally described in "Christie's Gas Chromatography and Lipids" (1989).

EXAMPLE 9

Anti-apoptotic Activity of Known Phospholipids

Figure 14:
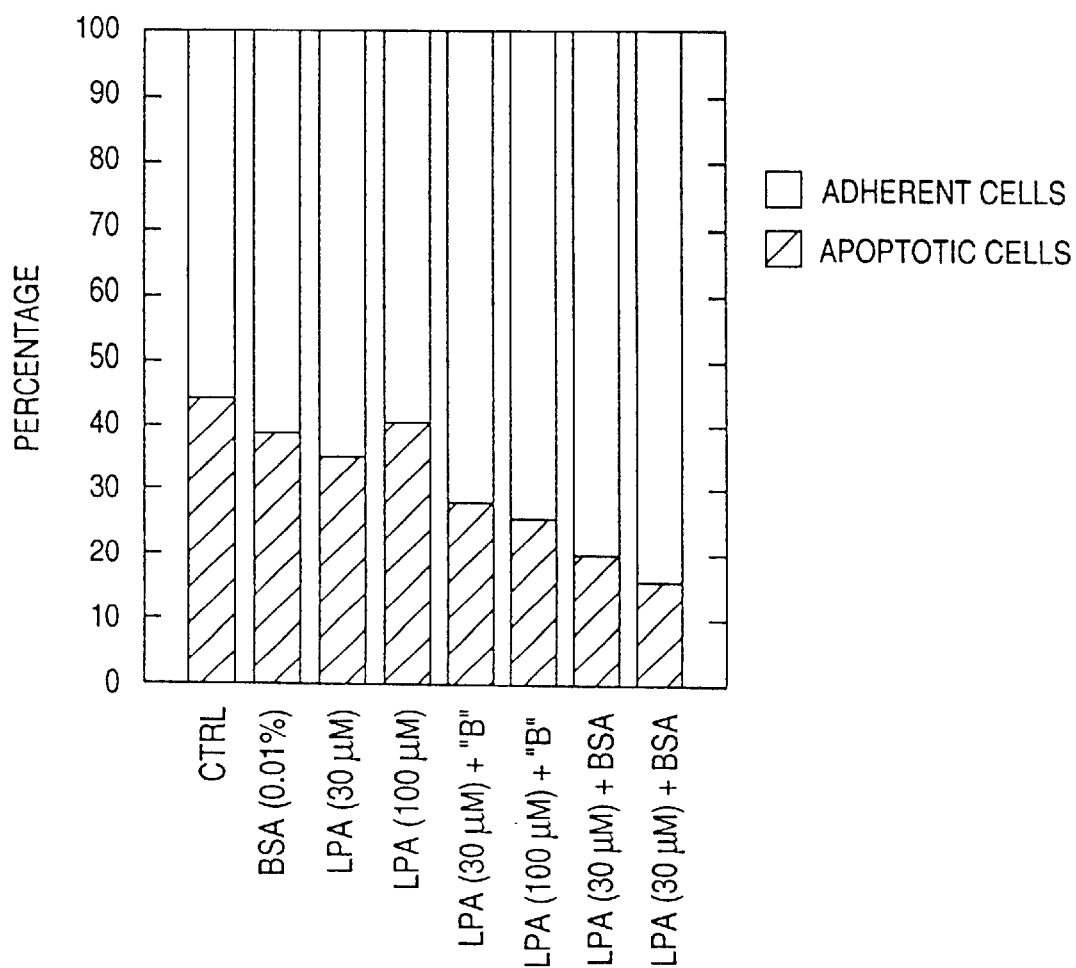
FIG. 14 is a bar graph depicting anti-apoptotic activity of lysophosphatidic acid as enhanced by preincubation with BSA or fraction B. The abbreviations used are: LPA, Lα-lysophosphatidic acid, oleoyl (C18:1, [cis]-9); BSA, bovine serum albumIn, fraction V, ethanol extracted; and "B," fraction B from soy flour, predominantly phosphatidyl inositol.
Figure 15:
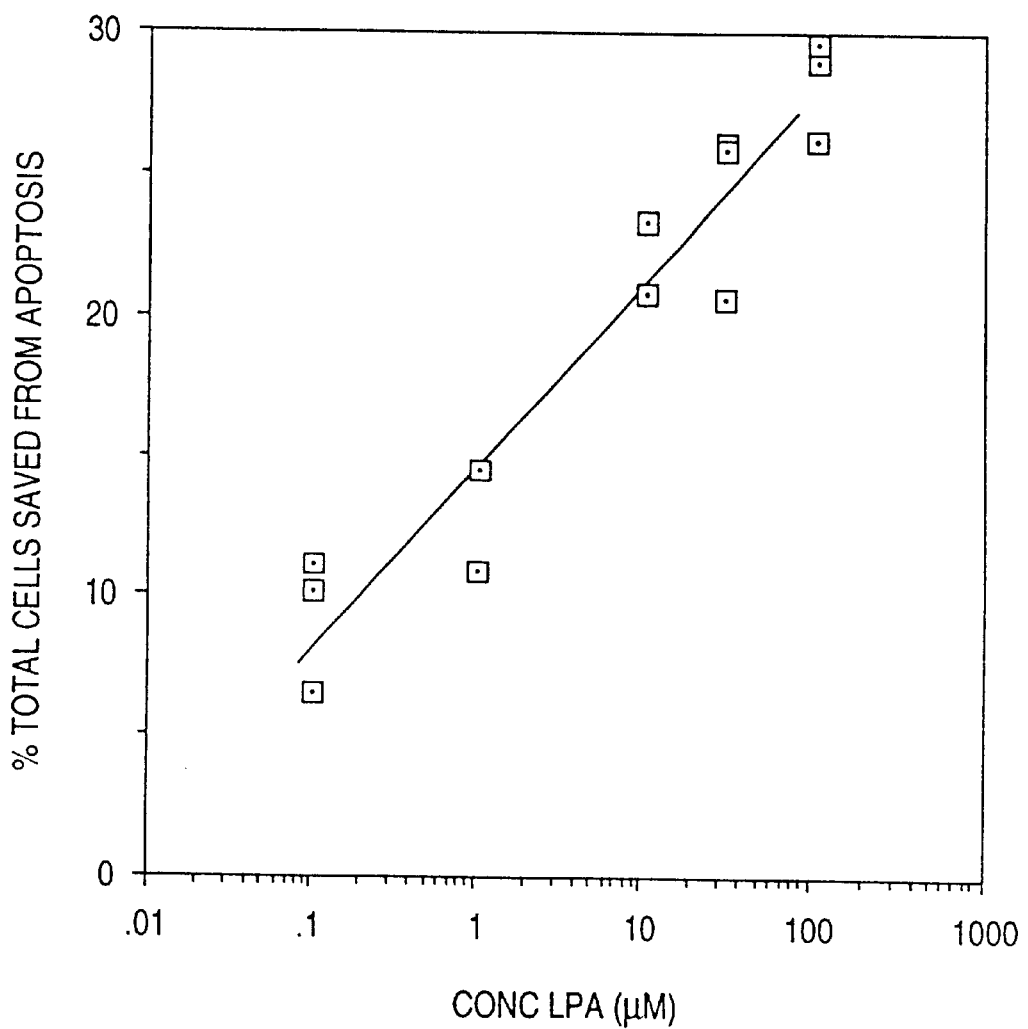
FIG. 15 is a graph depicting the anti-apoptotic effect of lysophosphatidic acid, oleoyl (C18:1, [cis]-9) on serum deprived C3H 10T½ cells in vitro.

Known phospholipid compounds were assayed for anti-apoptotic activity on serum-deprived 10T½ cells as described in Example 2. All commercial samples were dissolved at a concentration of 10 mM (100× test concentration) in 1% bovine serum albumin (BSA), 0.5 mM calcium chloride, 0.5 mM magnesium chloride, at room temperature. All compounds were tested after pre-incubation in 1% BSA. The final concentration of BSA in the apoptosis was ≦0.01%. Pre-incubation with BSA or fraction "B," which is mainly PI, enhanced the anti-apoptotic activity of LPA (FIG. 14). All tested compounds were obtained from Sigma. The BSA was obtained from Boehringer Mannheim. The results obtained are presented in Table 9 and FIG. 15.

TABLE 9

| COMPOUND | ACTIVITY |
| --- | --- |
| L-a-lysophosphatidic acid, oleoyl (C18:1, ** [cis]-9) | ++ |
| L-a-lysophosphatidyl-L-serine | ++ |
| L-a-lysophosphatidyl choline, Type VI | -- |
| L-a-lysophosphatidyl inositol ** | -- |
| L-a-lysophosphatidyl ethanolamine, Type IV | 0 |
| L-a-phosphatidic acid, dioleoyl (C18:1, [cis]-9) | 0 |
| L-a-phosphatidyl-L-serine, from bovine brain | 0 |
| L-a-phosphatidyl choline Type V-EA | 0 |
| L-a-phosphatidyl inositol ** | 0 |
| L-a-phosphatidyl ethanolamine, Type IV | 0 |

Key: ++ anti-apoptotic activity
0 no activity
-- apoptotic or necrotic effect
** compounds identified by mass spec., present in active fractions Although the foregoing invention has been described in some detail by way of illustration and example for purposes of clarity of understanding, it will be apparent to those skilled in the art that certain changes and modifications may be practiced. Therefore, the descriptions and examples should not be construed as limiting the scope of the invention, which is delineated by the appended claims.

We claim:

1. A method of obtaining a composition comprising a factor with anti-apoptotic activity wherein the method comprises the steps of
    a) delipidating a plant powder by extraction of the powder with a solution containing an organic solvent;
    b) separating the powder from the organic solvent;
    c) extracting the delipidated powder with an aqueous solution selected from the group consisting of (i) an aqueous solution comprising a water-miscible organic solvent at a concentration of up to 80% of the solution and (ii) phosphate buffered saline; and
    d) separating the aqueous solution from the delipidated powder to obtain an aqueous retentate composition comprising a factor with anti-apoptotic activity.

2. The method according to claim 1 wherein the plant powder is delipidated by extraction of the powder with an organic solvent selected from the group consisting of acetone, carbon tetrachloride, ether, hexane and chloroform.

3. The method according to claim 1, wherein the plant powder is obtained from any plant part.

4. The method according to claim 3, wherein the plant part is a storage organ.

5. The method according to claim 4, wherein the storage organ is selected from the group consisting of tubers, seeds and bulbs.

6. The method according to claim 1, wherein the plant powder is derived from the plant families of *leguminosae, solanum* and *allium*.

7. The method according to claim 6, wherein the plant powder is derived from pea or soybean seeds.

8. The method according to claim 6, wherein the plant powder is derived from potato tubers.

9. The method according to claim 1, wherein the aqueous solution is phosphate buffered saline.

10. The method according to claim 1, wherein the water-miscible organic solvents are selected from the group consisting of acetonitrile, lower alkanols, especially $C_1$–$C_4$ alkanols, lower alkanediols, $C_2$–$C_4$ alkanediols, and polymers of lower alkanediols.

11. The method according to claim 10, wherein the water-miscible organic solvent is ethanol.

12. The method according to claim 11, wherein the ethanol is present at a concentration of 50%.

13. The method according to claim 1, further comprising the step of removing the residual water-miscible organic solvent.

14. The method according to claim 13, wherein the step of removing the residual water-miscible organic solvent is by dialysis, ultrafiltration, or lyophilization.

15. The method according to claim 1, further comprising the step of precipitating contaminants of the aqueous retentate.

16. The method according to claim 1, further comprising the step of separating the composition from other components in the aqueous solution by subjecting the aqueous solution to size exclusion gel filtration chromatography.

17. The method according to claim 16, wherein the chromatographic agent employed is selected from the group consisting of Sepharose and BioGel.

18. The method according to claim 17, wherein the chromatographic agent employed is Sepharose S100HR.

19. The method according to claim 16, wherein a chromatography buffer is used and is selected from the group consisting of 0.1 to 0.3 M ammonium bicarbonate or 0.1 to 0.3 M sodium chloride, and 10 to 50 mM phosphate at neutral pH.

20. The method according to claim 19, wherein the chromatography buffer is comprised of 0.1 M ammonium bicarbonate.

21. The method according to claim 16, wherein fractions are collected from the gel filtration chromatography and the fractions with the greatest absorbance at 280 nm are collected and pooled.

22. The method according to claim 16, wherein fractions are collected from the gel filtration chromatography and the fractions with an apparent molecular weight of greater than 80 kD are collected and pooled.

23. The method according to claim 22, wherein fractions are collected from the gel filtration chromatography and those containing the composition are purified and concentrated by dialysis and lyophilization.

24. The method according to claim 23, further comprising the step of extracting the aqueous retentate with a single phase mixture of organic solvents and water to obtain an aqueous phase containing the composition and an organic phase.

25. The method according to claim 24, further comprising the step of lyophilizing the aqueous retentate.

26. The method according to claim 25, further comprising the steps of:
   a) extracting the lyophilized material with a single phase mixture of organic solvents and water; and
   b) isolating a glycolipid and phospholipid containing fraction by separating the insoluble material from the extracting mixture.

27. The method according to claim 26, wherein the single phase mixture of organic solvents and water comprises chloroform, methanol, and water.

28. The method according to claim 27, wherein the chloroform, methanol and water are present in a ratio of 4:8:3.

29. The method according to claim 26, wherein the separating of step b) is accomplished by a method selected from the group consisting of filtration or centrifugation.

30. The method according to claim 28, further comprising the step of separating by silica chromatography in a mixture of chloroform:methanol.

31. The method according to claim 30 further comprising the step of separating on a diol column.

32. The method according to claim 31 further comprising the step of performing HPLC separation on a silica column to obtain a flow through and five fractions.

33. A method of obtaining a composition with anti-apoptotic activity, comprising the steps of:
   a) obtaining a powder of dried peas;
   b) delipidating the powder with an organic phase comprising 70% acetone, wherein the organic phase is in a volume approximately equal to the weight of the powder;
   c) separating the acetone from the delipidated powder;
   d) extracting the delipidated powder with an aqueous phase comprising ethanol and water, wherein the aqueous phase is in a volume approximately equal to the weight of the delipidated powder;
   e) separating the aqueous phase from the extracted plant powder to obtain an aqueous retentate;
   f) removing the ethanol from the aqueous retentate by filtration; and
   g) lyophilizing the product of step f) to obtain a composition with anti-apoptotic activity.

34. The method according to claim 33, further comprising the steps of extracting the lyophilized product of step g) with a single phase mixture of chloroform, methanol, and water present in a ratio of 4:8:3; and isolating a lipid/glycolipid/phospholipid containing fraction separating the insoluble material from the extracting mixture by centrifugation.

35. A method of obtaining a composition comprising a factor with anti-apoptotic activity wherein the method comprises the steps of:
   a) delipidating a plant powder by extraction of the powder with a solution containing an organic solvent;
   b) separating the powder from the organic solvent;
   c) extracting the delipidated powder with an aqueous solution;
   d) separating the aqueous solution from the delipidated powder to obtain an aqueous retentate composition comprising a factor with anti-apoptotic activity; and
   e) precipitating contaminants of the aqueous retentate composition.

36. A method of obtaining a composition comprising a factor with anti-apoptotic activity wherein the method comprises the steps of:
   a) delipidating a plant powder by extraction of the powder with a solution containing an organic solvent;
   b) separating the powder from the organic solvent;
   c) extracting the delipidated powder with an aqueous solution;
   d) subjecting the aqueous solution to size exclusion chromatography to obtain an aqueous retentate composition comprising a factor with anti-apoptotic activity; and
   e) precipitating contaminants of the aqueous retentate composite.

* * * * *